United States Patent
Lu et al.

(10) Patent No.: US 7,179,468 B1
(45) Date of Patent: Feb. 20, 2007

(54) ANTIGEN FOR DEVELOPING NEUTRALIZING ANTIBODIES TO HUMAN IMMUNODEFICIENCY VIRUS

(75) Inventors: Min Lu, New York, NY (US); Hong Ji, New York, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 164 days.

(21) Appl. No.: 09/877,606

(22) Filed: Jun. 8, 2001

Related U.S. Application Data
(60) Provisional application No. 60/210,322, filed on Jun. 8, 2000.

(51) Int. Cl.
*A61K 39/21* (2006.01)

(52) U.S. Cl. .............................. 424/188.1; 424/192.1; 424/208.1; 530/300; 530/350

(58) Field of Classification Search .............. 424/188.1, 424/208.1, 192.1; 530/300, 350
See application file for complete search history.

(56) References Cited

U.S. PATENT DOCUMENTS

| | | | |
|---|---|---|---|
| 5,643,756 A | 7/1997 | Kayman et al. | ............. 435/697 |
| 5,654,195 A | 8/1997 | Sodroski et al. | .......... 435/320.1 |
| 5,714,577 A | 2/1998 | Montelaro et al. | ........... 530/324 |
| 5,854,037 A | 12/1998 | Palese et al. | ............. 435/172.3 |

FOREIGN PATENT DOCUMENTS

| | | |
|---|---|---|
| EP | 0679187 | 1/1994 |
| WO | WO-99/16883 | 4/1999 |

OTHER PUBLICATIONS

Lu, M., et al. (1995) "A trimeric structural domain of the HIV–1 transmembrane glycoprotein," *Nature Structural Biology*, vol. 12:1075–1082.

Blacklow, S.C., et al. (1995) "A Trimeric Subdomain of the Simian Immunodeficiency Virus Envelope Glycoprotain," *Biochemistry*, vol. 34(46):14955–14962.

Lu, M., et al. (1997) "A Trimeric Structural Subdomain of the HIV–1 Transmembrane Glycoprotein," *Journal of Biomolecular Structure & Dynamics*, vol. 15(3):465–471.

Chen, C.H., et al. (1995) "A Molecular Clasp in the Human Immunodeficiency Virus (HIV) Type 1 TM Protein Determines the Anti–HIV Activity of gp41 Derivatives: Implication for Viral Fusion," *Journal of Virology*, 3771–3777.

(Continued)

*Primary Examiner*—Jeffrey S. Parkin
(74) *Attorney, Agent, or Firm*—Schwegman, Lundberg, Woessner & Kluth, P.A.

(57) ABSTRACT

The present invention provides polypeptides comprising a stabilized trimer of the carboxyl-terminal core region of the ectodomain of an enveloped virus, such as HIV. A subject polypeptide comprises three monomers that form a trimeric coiled coil in a prefusogenic conformation of an enveloped virus such as HIV. The subject polypeptides are useful as vacciness against enveloped virus, such as HIV, which vaccines are also provided. The present invention also provides methods of vaccinating an individual to prevent or treat HIV infection or prevent or treat infection by another enveloped virus, using a subject vaccine. Antibodies or binding portions thereof raised against a C-terminus trimeric coiled coil motif of an HIV gp41 ectodomain, or carboxyl-terminal core region of the ectodomain of another enveloped virus, are also provided as are methods of making such antibodies. Methods for detecting HIV or other enveloped viruses in a sample, as well as methods of screening for drugs which can inhibit HIV infection or other enveloped virus infection, are also provided by the present invention.

11 Claims, 8 Drawing Sheets

OTHER PUBLICATIONS

Tan, K., et al. (1997) "Atomic Structure of a thermostable subdomain of HIV–1 gp41," *Proc. Natl. Acad. Sci. USA*, vol. 94:12303–12308.

Salzwedel, K., et al. (1999) "A Conserved Tryptophan–Rich Motif in the Membrane–Proximal Region of the Human Immunodeficiency Virus Type 1 gp41 Ectodomain Is Important for Env–Mediated Fusion and Virus Infectivity," *Journal of Virology*, vol. 73(3):2469–2480.

Jiang, et al. (1993) "HIV–1 inhibition by a peptide" and "Nested fullerene–like structures," *Scientific Correspondence*, vol. 365:113.

Malashkevich, V.N., et al. (1998) "Crystal structure of the simian immunodeficiency virus (SIV) gp41 core: Conserved helical interactions underlie the broad inhibitory activity of gp41 peptides," *Proc. Natl. Acad. Sci. USA*, vol. 95:9134–9139.

Wild, C.T., et al. (1994) "Peptides corresponding to a predictive –helical domain of human immunodeficiency virus type 1 gp41 are potent inhibitors of virus infection," *Proc. Natl. Acad. Sci USA*, vol. 91:9770–9774.

Gallaher, W.R., et al. (1989) "A General Model for the Transmembrane Proteins of HIV and Other Retroviruses," *AIDS Research and Human Retroviruses*, vol. 5(4):431–440.

Chambers, P., et al. (1990) "Heptad repeat sequences are located adjacent to hydrophobic regions in several types of virus fusion glycoproteins," *Journal of General Virology*, 71:3075–3080.

Wild, C., et al. (1995) "The Inhibitory Activity of an HIV Type 1 Peptide Correlates with Its Ability to Interact with a Leucine Zipper Structure," *AIDS Research and Human Retroviruses*, vol. 11(3):323–325.

Delwart, E.L., et al. (1990) "Retroviral Envelope Glycoproteins Contain a 'Leucine Zipper'–like Repeat," *AIDS Research and Human Retroviruses*, vol. 6(6):703–706.

Neurath, A.R., et al. (1995) "Two Partially Overlapping Antiviral Peptides from the External Portion of HIV Type 1 Glycoprotein 41, Adjoining the Transmembrane Region, Affect the Glycoprotein 41 Fusion Domain," *AIDS Research and Human Retroviruses*, vol. 11(2):189–190.

Chan, D.C., et al. (1997) "Core Structure of gp41 from the HIV Envelope Glycoprotein," *Cell*, vol. 89:263–273.

Caffrey, et al. (1998) "Three–dimensional solution structure of the 44 kDa ectodomain of SIV gp41," *The EMBO Journal*, vol. 17(16):4572–4584.

Yang, X., et al. (2000) "Modifications That Stabilize Human Immunodeficiency Virus Envelope Glycoprotein Trimers in Solution," *Journal of Virology*, vol. 74(10):4746–4754.

Yang, Z.N., et al. (1999) "The Crystal Structure of the SIV gp41 Ectodomain at 1.47 A Resolution," *Journal of Structural Biology*, 126:131–144.

Weissenhorn, W., et al. (1997) "Atomic structure of the ectodomain from HIV–1 gp41," *Nature*, vol. 387(22):426–430.

Blacklow, Stephen.C. ,et al. ,"A Trimeric Subdomain of the Simian Immunodeficiency Virus Envelope Glycoprotein", *Biochemistry*, (1995),14955–14962.

Chan, David.C. ,et al. ,"Core Structure of gp41 from the HIV Envelope Glycoprotein", *Cell*, (Apr. 1997),263–273.

Chan, David.C. ,et al. ,"Evidence that a prominent cavity in the coiled coil of HIV type 1 gp41 is an attractive drug target", *Proceedings of the National Academy of Sciences of the United States of America*, (Dec. 1998),15613–15617.

Chen, Chin–Ho.,et al. ,"A Molecular Clasp in the Human Immunodeficiency Virus (HIV) Type 1 TM Protein Determines the Anti–HIV Activity of gp41 Derivatives: Implication for Viral Fusion", *Journal of Virology*, (Jun. 1995), 3771–3777.

Furuta, Rika.A. ,et al. ,"Capture of an early fusion–active conformation of HIV–1 gp41", *Nature Structural Biology*, (Apr. 1998),276–279.

Kilby, J.M. ,et al. ,"Potent suppression of HIV–1 replication in humans by T–20, a peptide inhibitor of gp41–mediated virus entry", *Nat Med*, (Nov. 1998),Abstract.

Lawless, M.K. ,et al. ,"HIV–1 membrane fusion mechanism: structural studies of the interactions between biologically–active peptides from gp41", *Biochemistry*, (Oct. 1996), Abstract.

Lawless, M.K. ,et al. ,"Quantitation of a 36–amino–acid peptide inhibitor of HIV–1 membrane fusion in animal and human plasma using high–performance liquid chromatography and fluorescence detection", *J Chromatogr & Biomed Sci Appl*, (Apr. 1998),Abstract.

Lu, Min.,et al. ,"A trimeric structural domain of the HIV–1 transmembrane glycoprotein", *Nature Structural Biology*, (Dec. 1995),1075–1082.

Rabenstein, Mark.,et al. ,"A Peptide from the Heptad Repeat of Human Immunodeficiency Virus gp41 Shows both Membrane Binding and Coiled Coil Formation", *Biochemistry*, (1995),13390–13397.

Shu, Wei.,et al. ,"Trimerization Specificity in HIV–1 gp41: Analysis with a GCN4 Leucine Zipper Model", *Biochemistry*, (1999),5378–5385.

Shurgas, Diane.C. ,et al. ,"Biophysical Characterization of Recombinant Proteins Expressing the Leucine Zipper–Like Domain of the Human Immunodeficiency Virus Type 1 Transmembrane Protein gp41", *Journal of Virology*, (May 1996),2982–2991.

Tan, Kemin.,et al. ,"Atomic structure of a thermostable subdomain of HIV–1 gp–42", *Proceedings of the National Academy of Sciences of the United States of America*, (Nov. 1997),12303–12308.

Vazquez, Maria–Isabel.,et al. ,"The Vaccinia Virus 14–Kilodalton (A27L) Fusion Protein Forms a Triple Coiled–Coil Structure and Interacts with the 21–Kilodalton (A17L) Virus Membrane Protein through a C–Terminal a–Helix", *Journal of Virology*, (Dec. 1998),10126–10137.

Weissenhorn, Winfried.,et al. ,"Assembly of a rod–shaped chimera of a trimeric GCN4 zipper and the HIV–1 gp41 ectodomain expressed in *Escherichia coli* ", *Proceedings of the National Academy of Sciences of the United States of America*, (Jun. 1997),6065–6069.

Weissenhorn, W.,et al. ,"Atomic structure of the ectodomain from HIV–1 gp41", *Nature*, (May 1997),426–430.

Weng, Yongkai.,et al. ,"Mutational Analysis of Residues in the Coiled–Coil Domain of Human Immunodeficiency Virus Type 1 Transmembrane Protein gp41", *Journla of Virology*, (Dec. 1998),9676–9682.

Wild, Carl.,et al. ,"Propensity for a leucine zipper–like domain of human immunodeficiency virus type 1 gp41 to form oligomers correlates with a role in virus–induced fusion rather than assembly of the glycoprotein complex", *Proceedings of the National Academy of Sciences of the United States of America*, (Dec. 1994),12676–12680.

Shu, Wei, "Helical Interactions in the HIV–1 gp41 Core Reveal Structural Basis for the Inhibitory Activity of gp41 Peptides", *Biochemistry*, 39(7), (Feb. 22, 2000), 1634?1642

| 669 | 670 | 671 | 672 | 673 | 674 | 675 |
|---|---|---|---|---|---|---|
| L 205 | W 210 | N 163 | W 212 | F 204 | D 129 | I 212 |
| I 6 | • 3 | S 39 | • 1 | L 7 | S 46 | M 1 |
| V 1 |  | T 10 |  | Y 1 | N 23 |  |
| S 1 |  | D 1 |  | S 1 | G 9 |  |
|  |  |  |  |  | T 3 |  |
|  |  |  |  |  | E 2 |  |
|  |  |  |  |  | • 1 |  |

Figure 8

ANTIGEN FOR DEVELOPING NEUTRALIZING ANTIBODIES TO HUMAN IMMUNODEFICIENCY VIRUS

This application claims priority from U.S. Provisional Application, Ser. No. 60/210,322, filed Jun. 8, 2000, which is hereby incorporated by reference.

The invention described herein was made under a grant from the National Institutes of Health, Grant No. AI42382-01A1. The Government may have certain rights in the invention.

BACKGROUND OF THE INVENTION

Infection of cells by HIV-1 is initiated by fusion of the viral and cellular membranes, a process mediated by the envelope glycoprotein on the surface of the virion. The HIV-1 envelope glycoprotein, gp160, is posttranslationally cleaved into two noncovalently associated subunits, gp120 and gp41 (1). The envelope glycoprotein complex consists of a trimer of three gp120 surface subunits and three gp41 transmembrane subunits. Analysis of its structure by X-ray crystallography shows that the $NH_2$-terminal region of the ectodomain of gp41 forms a central, three-stranded coiled coil that is wrapped by an outer layer of three COOH-terminal helices in an antiparallel orientation around the outside of the coiled coil (6).

Each gp41 chain is anchored at its COOH terminus in the viral membrane. gp 120 determines viral tropism by binding to the cellular receptors, CD4 and members of the chemokine receptor family, whereas gp41 is responsible for fusing the viral and host cell membranes (2). There is substantial evidence to indicate that receptor binding triggers conformational changes in the gp120/gp41 complex, leading to activation of gp41 membrane fusion properties and ultimately invasion of the viral genome (3). By analogy with the 'spring-loaded' model of the influenza virus hemagglutinin (4), gp41 activation is postulated to involve a complex set of structural changes from a native (prefusogenic) state to a fusion-active (fusogenic) conformation (5).

Because the membrane anchor and the $NH_2$-terminal fusion peptide of gp41 are embedded in the viral and target cell membranes respectively, formation of the trimer-of-hairpins structure is thought to appose two membranes for fusion (7). A monoclonal antibody recognizing this gp41 core binds specifically to the surface of HIV-1 infected cells only after addition of soluble CD4 (8). This observation provides direct evidence that the trimer-of-hairpins structure represents the fusion-active state of gp41 (6). The structure of the HIV-1 envelope glycoprotein in its native conformation is unknown.

The viral envelope glycoprotein that mediates HIV-1 entry into target cells is an important target for humoral immunity during the natural course of infection (30). Current recombinant gp120 or gp41 protein vaccine candidates are unable to elicit antibodies capable of neutralizing primary HIV-1 isolates from infected persons at sigpificant titers (34). These antibodies bind well to the individual gp120 and gp41 subunits but poorly to the membrane-associated, native envelope glycoprotein complex (FIG. 1) (35). In contrast, three infected human-derived neutralizing antibodies have been shown to recognize the native gp120/gp41 complex efficiently (10). Thus, it appears that an immune response to virions, rather than to nonnative forms of the envelope glycoprotein (called viral debris), leads to the production of functional antibodies. Since gp120 is readily dissociated or shed from gp41 (37), the challenge of inducing protective humoral immunity is to preserve the native envelope structure, or crucial components thereof, in vaccine preparations.

Because inhibition of gp41-mediated membrane fusion has potential to offer a general strategy for the treatment or prevention of HIV-1 infection (9), structural information on the conformational change of the protein is crucial to guiding efforts to target this process for vaccine and antiviral drug development. In accordance with the present invention, it has been discovered that a peptide fragment derived from the COOH-terminal region of the gp41 ectodomain, forms a parallel three-stranded, α-helical coiled coil and serves as a trimerization domain in the native gp120/gp41 complex. A stable form of the trimeric coiled-coil domain elicits a strong antiviral antibody response against HIV-1 primary isolates from AIDS patients and thus has utility as a safe and practical HIV-1 vaccine immunogen.

SUMMARY OF THE INVENTION

The present invention provides polypeptides comprising a stabilized HIV gp41 trimer. A subject polypeptide comprises three gp41 monomers that form a trimeric coiled coil, in a prefusogenic conformation.

In one embodiment of the invention, the trimer is stabilized by using an isoleucine zipper. In another embodiment of the invention, the trimer is stabilized by chemical cross-linking of gp41 monomers. In yet another embodiment of the invention, the trimer is stabilized by point mutations in gp41 monomers. The subject polypeptides may be synthetically or recombinantly produced.

In another aspect of the invention, there is provided a vaccine for the prevention or treatment of HIV infection or AIDS. The vaccine comprises a stabilized HIV gp41 trimer, comprising three gp41 monomers that form a trimeric coiled coil, in a prefusogenic conformation. The vaccine may be synthetically or recombinantly produced and may also comprise a suitable adjuvant.

In still another aspect of the invention, there is provided a method of vaccinating an individual to prevent or treat HIV infection or AIDS. The method comprises administering to the individual an immunogenically effective amount of a composition comprising a subject vaccine. A subject vaccine may be administered in combination with a physiologically acceptable carrier or diluent.

Also provided by the present invention is an antibody or binding portion thereof raised against a C terminus trimeric coiled coil motif of an HIV gp41 ectodomain. The antibody or binding portion thereof may be monoclonal or polyclonal.

In a further aspect of the invention, there is provided a method of detecting HIV in a sample. The method comprises the steps of exposing a sample to a subject antibody or binding portion thereof, and identifying binding between HIV and the antibody or binding portion.

A method of making a subject antibody or binding portion thereof is also provided. The method comprises exposing an antibody-producing cell to an isolated HIV gp41 trimer comprising three gp41 monomers that form a trimeric coiled coil, in an inactive conformation, under conditions effective to produce the antibody or binding portion thereof. Examples of antibody-producing cells for use in the method include e.g. cultured hybridoma cells and cells present in a living organism.

A method of inhibiting HIV infectivity is also provided. The method comprises contacting HIV with a suitable amount of a subject antibody or binding portion thereof under conditions effective to inhibit HIV infectivity. A subject antibody or binding portion thereof may be administered to a host before or following exposure of the host to an infective HIV strain.

In yet another aspect of the present invention, a method of screening for drugs which inhibit HIV infection is provided. The method comprises the steps of providing a gp41 trimer comprising three gp41 monomers that form a trimeric coiled coil in a prefusogenic conformation; exposing the trimer to a compound; and identifying those compounds which bind to the gp41 trimer. Preferably, a determination is made as to whether gp41 bound to the compound binds less effectively to gp120 than gp41 not bound to the compound.

In addition to HIV, the present invention is also directed to polypeptides comprising a stabilized viral envelope protein from other enveloped viruses. Thus, there are provided polypeptides comprising a stabilized viral envelope protein trimer wherein the trimer comprises a C-terminal heptad repeat region of the ectodomain in a prefusogenic conformation. Examples of other enveloped viruses include but are not limited to SIV, Mo-MLV, influenza virus, and Ebola virus.

The present invention also provides vaccines comprising such stabilized viral envelope protein trimers, methods of vaccinating an individual to prevent or treat infection by an enveloped virus, antibodies (or binding portions thereof) raised against polypeptides comprising a stabilized viral envelope protein trimer, methods of making such antibodies or binding portions thereof, methods of inhibiting infectivity of an enveloped virus, and methods for screening for drugs which can inhibit infection by an enveloped virus.

BRIEF DESCRIPTION OF THE DRAWINGS

FIG. 8 shows the frequency of occurrence of amino acids at positions 669 to 675 of gp160 (SEQ ID NO:5 and SEQ ID NO:8). The sequences of 213 fully sequenced M group HIV-1 strains (HIV Sequence Database [1998/1999 alignments], Los Alamos National Laboratory, http:hiv-web.lanl.gov) were analyzed. The amino acids occurring at positions 669 to 675 are shown with the number of times they occur at these positions. Periods indicate stop codons.

DETAILED DESCRIPTION OF THE INVENTION

In accordance with the present invention, it has been discovered that favorable presentation of the gp41 COOH-terminal coiled-coil region of HIV is important for inducing antibodies that neutralize representative primary HIV-1 isolates in primary cell cultures. The present invention therefore overcomes three major obstacles in ongoing HIV-1 vaccine development. In the first instance, a natural infection with HIV-1 stimulates only weak functional antibody responses, most likely because the trimeric envelope glycoprotein spikes are poorly immunogenic (30). In accordance with the present invention, a stable trimerization domain of the native gp120/gp41 complex acts as an immunogen that provokes a highly focused and strong humoral immune response. In addition, antibodies produced in natural infection or typical vaccination protocols bind weakly to primary clinical isolates and are therefore of limited efficacy in controlling the virus (35). Through immunization with a stable form of a surface-exposed gp41 coiled coil, provided by the present invention, neutralizing antibodies have been generated which bind to primary viruses. Further, the ability to constantly select for viral variants is a defense mechanism by which HIV-1 resists or evades humoral immunity after either natural or experimental infection or envelope-based vaccination. In accordance with the present invention, the preservation of a well-conserved envelope protein structure in vaccine candidates as described herein is useful in surmounting the barrier of viral antigenic variation and thus preventing an initial HIV-1 infection.

Figure 1:
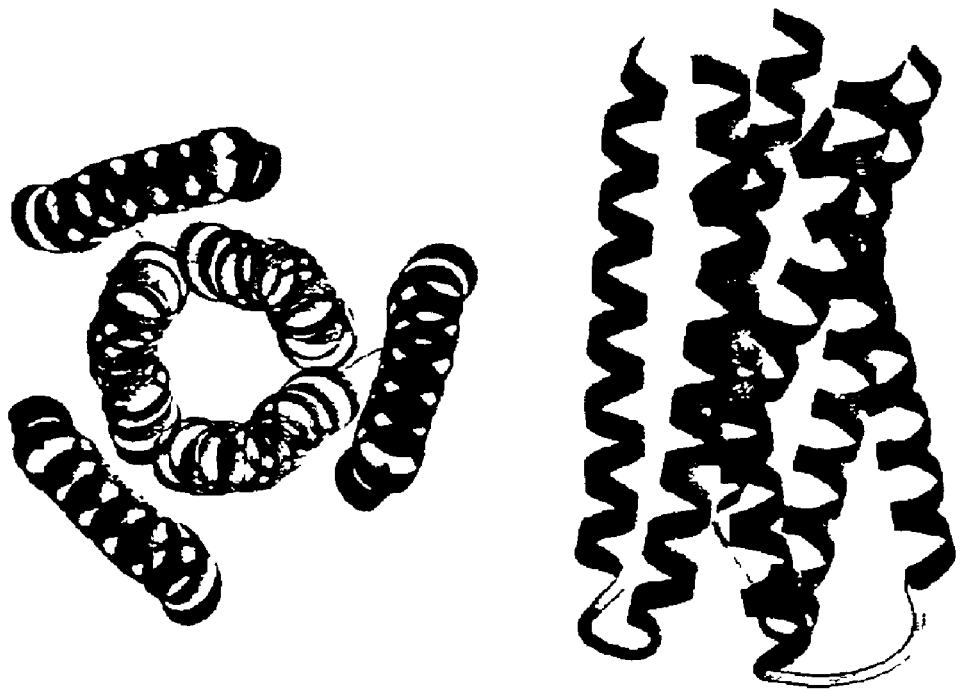
FIG. 1 illustrates the trimer-of-hairpins structure of fusion-active gp41. The axial and side views of the gp41 core structure are shown (6). The $NH_2$-terminal helices (blue) form an interior trimeric coiled coil, surrounded by an outer layer of three antiparallel COOH-terminal helices (red). This molecular arrangement is thought to force the viral and cellular membranes close together and thus overcome the energy barrier for membrane fusion (7).

The ectodomain core structures of the membrane fusion subunits from many enveloped viruses, including but not limited to HIV-1, HIV-2, SIV, Mo-MLV, influenza virus, and Ebola virus, are remarkably similar (reviewed in Chan & Kim, 1999; Skehel & Wiley, 1998). In all cases, an interior, trimeric coiled coil (formed by the N-terminal heptad-repeat regions) is surrounded by helices derived from the C-terminal end of the ectodomains, packed in an antiparallel manner around the outside of the coiled coil (see FIG. 1). A large body of evidence suggests that viral fusion proteins undergo a similar conformational change to become fusion active (Chan, D. C. & Kim, P. S., 1988 "HIV entry and its inhibition," Cell 93: 681–684; Skehel, J. J. & Wiley, D. C., 1998 "Coiled coils in both intracellular vesicle and viral membrane fusion," Cell 95: 871–874). Thus, the flip-flop molecular mechanism for activation and refolding of the viral membrane fusion protein is likely to be a general mechanism of infection by enveloped viruses. The C-terminal heptad-repeat regions of other viral fusion proteins such as those found in SIV, Mo-MLV, and Ebola virus also likely form trimerization and folding domains in their prefusogenic conformations.

In a first aspect of the invention, there is provided a polypeptide comprising a stabilized viral envelope protein trimer. The protein trimer comprises a C-terminal heptad repeat region of the ectodomain in a prefusogenic conformation. Examples of enveloped viruses from which a subject polypeptide may be derived include, but are not limited to HIV-1, HIV-2, SIV, Mo-MLV, influenza virus, and Ebola virus.

In a preferred embodiment, a subject polypeptide comprises a stabilized HIV gp41 trimer comprising three gp41 monomers that form a trimeric coiled coil in a prefusogenic conformation. In accordance with the present invention, such a polypeptide may be obtained by isolating and stabilizing the carboxyl-terminal core region of the gp41 ectodomain. The terms "carboxyl-terminal core region of the gp41 ectodomain" and "C-terminus trimeric coiled coil motif of an HIV gp41 ectodomain" are used interchangeably herein. The terms "prefusogenic" and "native" are also used interchangeably herein in describing a subject stabilized HIV gp41 trimer or other viral envelope protein trimer.

Conventional recombinant schemes may be used to obtain an isolated polypeptide comprising a stabilized viral envelope protein trimer, wherein the trimer comprises a C-terminal heptad repeat region of the ectodomain in a prefusogenic conformation. The nucleic acid and amino acid sequences of different envelope proteins are known. For example, the nucleic acid and amino acid sequences for HIV-1, HIV-2, and SIV may be found in the HIV Sequence Database, Human Retrovirus and AIDS, 2000 ed., Los Alamos National Laboratory. The nucleotide and amino acid sequences for Mo-MLV, influenza virus, and Ebola virus, as well as other enveloped viruses, are available through Medline (www.ncbi.nlm.nih.gov/pubmed). These disclosures, as well as all other published references cited herein, are incorporated by reference as if fully set forth. The C-terminal heptad repeat region of the ectodomain of enveloped viruses is easily discernible from the published sequences.

Similarly, conventional recombinant schemes may be used to obtain the isolated HIV gp41 trimer. In addition to the HIV Sequence Database and Medline, the complete nucleotide sequences of the HIV viruses had been previously reported by several investigators (Ratner et al., "Complete Nucleotide Sequence of the AIDS virus, HTLV-III," Nature 313:277–84 (1985); Muesing et al., "Nucleic Acid Structure and Expression of the Human AIDS/lymphadenopathy Retrovirus," Nature 313:450–458 (1985); Wain-Hobson et al., "Nucleotide Sequence of the AIDS Virus, LAV," Cell 40:9–17 (1985), which are hereby incorporated by reference). The RNA of the HIV-1 and HIV-2 viruses possess the following gene regions: so-called long terminal repeats at each end of the genome, gag, pol, env, and nef. The gag gene encodes the core proteins p24 and p17. The pol gene encodes the reverse transcriptase, RNAse H, and integrase. The gene nef encodes a protein having a regulatory function. The env gene encodes the glycoproteins of the viral coat, namely gp41 and gp120. The env gene has been associated particularly with antigenicity and infectivity.

Given the knowledge of nucleic acid sequences encoding HIV, as well as other enveloped viruses, one of ordinary skill in the art can readily insert coding sequence for the gp41 glycoprotein or other viral envelope trimer comprising a C-terminal heptad repeat region of the ectodomain in a prefusogenic conformation, directly into a host cell or into an intermediate expression vector. Coding sequences corresponding to the HIV gp41 glycoprotein are readily available and may be obtained e.g., from the NIH AIDS Research and Reference Reagent Program Catalogue, Rockville, Md. Coding sequences for other enveloped viruses may be obtained from sources such as the American Type Culture Collection (ATCC), Manassas, Va.

Various truncated fragments of the nucleotide sequence encoding the gp41 glycoprotein may be used in accordance with the present invention. For example, coding sequence corresponding to amino acid residues 536–666, 640–658, or 624–669 (numbered according to their position in gp160, the HXB2 HIV-1 strain) may be used. Fragments of the gp41 glycoprotein may be obtained by truncating the 5', 3', or both 5'and 3'ends of the gp41 coding sequence by genetic manipulation. In vitro mutagenesis is helpful for introducing restriction sites. Similarly, truncated fragments of other enveloped virus C-terminal heptad repeat regions of the ectodomain may be used. There are various commercially available kits particularly suited for this application such as the T7-Gene in vitro Mutagenesis Kit (USB, Cleveland, Ohio) and the QuickChange Site Directed Mutagenesis Kit (Stratagene, San Diego, Calif.). Alternatively, PCR primers can be derived to allow direct amplification of a particular portion of a gp41 coding sequence or C-terminal heptad repeat region.

The carboxyl-terminal core region of the gp41 ectodomain (C-terminus trimeric coiled coil motif of an HIV gp41 ectodomain) may be stabilized by e.g., insertion of an isoleucine zipper. The C-terminal heptad-repeat regions of the ectodomain of other enveloped viruses may also be stabilized by insertion of an isoleucine zipper. Thus, for example, an isoleucine zipper described in P. B. Harbury, et al. (1994) *Nature* 371:80, may be inserted near the C-terminus of the coiled coil segment. Preferably, the isoleucine zipper is inserted in heptad register and before residue 684 in HIV (residues numbered according to their position in gp 160, the HXB2 HIV-1 strain), which residue immediately precedes the transmembrane anchor. An isoleucine zipper may be inserted anywhere between residues 670 and 684 in HIV. Alternatively, an isoleucine zipper may be placed near the N-terminus of the C-terminal trimeric coiled coil of an HIV ectodomain or near the N-terminus of a C-terminal heptad-repeat region of the ectodomain of other enveloped viruses.

The carboxyl-terminal core region of the gp41 ectodomain may also be stabilized by cross linking of gp41 monomers. Similarly, the C-terminal heptad repeat regions of the ectodomain of other viral envelope proteins may be stabilized by cross linking. Such cross linking can be accomplished using well known methods such as those described in Houston, M. E., Jr. et al., (1995) *J. Peptide Science* 1:274–282.

The carboxyl-terminal core region of the gp41 ectodomain may also be stabilized by introducing one or point mutations in one or more gp41 monomers. Thus for example, Ser-649, Gln-652, Asn-656, and Glu-659 (numbered according to their position in gp160 in the HXB2 HIV-1 strain) may be mutated to the hydrophobic residue isoleucine. Methods of inducing point mutations are well known and include e.g., single stranded mutagenesis as described in T. A. Kunkel, et al., *Methods Enzymol.* 154, 367 (1987). The C-terminal heptad repeat region of the ectodomain of other enveloped viruses may also be stabilized by introducing one or more point mutations therein. Any and all possible mutations are contemplated by the present invention as long as the mutation does not destabilize the HIV trimer comprising three gp41 monomers which form a trimeric coiled coil in a prefusogenic conformation or does not destabilize a trimer comprising a C-terminal heptad-repeat region of the ectodomain in a prefusogenic conformation, of another enveloped virus.

Various expression vectors are known in the art, including plasmids, viral vectors, and bacteriophage vectors. The host cell to be transformed with the nucleic acid molecule may be most amenable to transformation with a particular type of expression vector. Plasmid vectors readily transform bacterial host cells. Viral vectors readily transform many mammalian cells.

A nucleic acid molecule coding for a subject polypeptide may be inserted into an expression vector using standard cloning procedures readily known in the art. This generally involves the use of restriction enzymes and DNA ligases, as described by Maniatis et al. (1982). U.S. Pat. No. 4,237,224 to Cohen and Boyer, which is hereby incorporated by reference, describes the production of expression systems in the form of recombinant plasmids using restriction enzyme cleavage and ligation with DNA ligase. These recombinant plasmids are then introduced by means of transformation and replicated in unicellular cultures including prokaryotic organisms and eukaryotic cells grown in tissue culture.

Suitable vectors include, but are not limited to, the following viral vectors such as lambda vector system gt11, gt WES.tB, Charon 4, and plasmid vectors such as pBR322, pBR325, pACYC177, pACYC1084, pUC8, pUC9, pUC18, pUC19, pLG339, pR290, pKC37, pKC101, SV 40, pBluescript II SK +/− or KS +/− (see “Stratagene Cloning Systems” Catalog (1993) from Stratagene, La Jolla, Calif., which is hereby incorporated by reference), pQE, pIH821, pGEX, pET series (see F. W. Studier et. al., “Use of T7 RNA Polymerase to Direct Expression of Cloned Genes,” Gene Expression Technology vol. 185 (1990), which is hereby incorporated by reference), and any derivatives thereof. Recombinant molecules can be introduced into cells via transformation, particularly transduction, conjugation, mobilization, or electroporation. The DNA sequences are cloned into the vector using standard cloning procedures in the art, as described by Sambrook et al., Molecular Cloning: A Laboratory Manual, Cold Springs Laboratory, Cold Springs Harbor, N.Y. (1989), which is hereby incorporated by reference.

A variety of host-vector systems may be utilized to express the protein-encoding sequence(s). Preferred vectors include a viral vector, plasmid, cosmid or an oligonucleotide. Primarily, the vector system must be compatible with the host cell used. Host-vector systems include but are not limited to the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus); and plant cells infected by bacteria. The expression elements of these vectors vary in their strength and specificities. Depending upon the host-vector system utilized, any one of a number of suitable transcription and translation elements can be used.

Different genetic signals and processing events control many levels of gene expression (e.g., DNA transcription and messenger RNA (mRNA) translation). Transcription of DNA is dependent upon the presence of a promotor which is a DNA sequence that directs the binding of RNA polymerase and thereby promotes mRNA synthesis. The DNA sequences of eukaryotic promoters differ from those of prokaryotic promoters. Furthermore, eukaryotic promoters and accompanying genetic signals may not be recognized in or may not function in a prokaryotic system, and, further, prokaryotic promoters are not recognized and do not function in eukaryotic cells.

Similarly, translation of mRNA depends upon the presence of the proper signals. Efficient translation of mRNA requires a ribosome binding site. This sequence is a short nucleotide sequence of mRNA that is located before the start codon, usually AUG, which encodes the amino-terminal methionine of the protein. The ribosome binding sites are complementary to the 3'-end of the 16S rRNA (ribosomal RNA) and probably promote binding of mRNA to ribosomes by duplexing with the rRNA to allow correct positioning of the ribosome. For a review on maximizing gene expression, see Roberts and Lauer, Methods in Enzymology, 68:473 (1979), which is hereby incorporated by reference.

A preferred embodiment of the invention is where the gene is functionally linked to a promoter. Promoters vary in their "strength" (i.e. their ability to promote transcription). For the purposes of expressing a cloned gene, it is desirable to use strong promoters in order to obtain a high level of transcription and, hence, expression of the gene. Depending upon the host cell system utilized, any one of a number of suitable promoters may be used. For instance, when cloning in E. coli, its bacteriophages, or plasmids, promoters such as the T7 phage promoter, lac promoter, trp promoter, recA promoter, ribosomal RNA promoter, the PR and PL promoters of coliphage lambda and others, including but not limited, to lacUV5, ompF, bla, lpp, and the like, may be used to direct high levels of transcription of adjacent DNA segments. Additionally, a hybrid trp-lacUV5 (tac) promoter or other E. coli promoters produced by recombinant DNA or other synthetic DNA techniques may be used to provide for transcription of the inserted gene.

Once the isolated nucleic acid molecule encoding the HIV gp41 glycoprotein or C-terminal heptad repeat of another enveloped virus, has been cloned into an expression system, it is ready to be incorporated into a host cell. Such incorporation can be carried out by the various conventional forms of transformation, including those dependent upon the vector/host cell system. Suitable host cells include, but are not limited to, bacteria, virus, yeast, mammalian cells, insect, and the like.

Biological markers can be used to identify the cells carrying recombinant DNA molecules. In bacteria, these are commonly drug-resistance genes. Drug resistance is used to select bacteria that have taken up cloned DNA from the much larger population of bacteria that have not. In the early mammalian gene transfer experiments involving viral genes, the transfer of exogenous DNA into cells was detected because the DNA had a biological activity, it led to production of infectious virus or produced stable changes in the growth properties of the transfected cells. It was then discovered that the DNA tumor virus, herpes simplex virus (HSV), contained a gene encoding the enzyme thymidine kinase (the tk gene). The HSV tk gene can be used as a selectable genetic marker in mammalian cells in much the same way that drug-resistance genes worked in bacteria, to allow rare transfected cells to grow up out of a much larger population that did not take up any DNA. The cells are transferred to selective growth medium, which permits growth only of cells that took up a functional tk gene (and the transferred DNA of interest). Various dominant selectable markers are now known in the art, including: aminoglycoside phosphotransferase (APH), using the drug G418 for selection which inhibits protein synthesis; the APH inactivates G418; dihydrofolate reductase (DHFR):Mtx-resistant variant, using the drug methotrexate (Mtx) for selection which inhibits DHFR; the variant DHFR is resistant to Mtx; hygromycin-B-phosphotransferase (HPH), using the drug hygromycin-B which inhibits protein synthesis; the HPH inactivates hygromycin B; thymidine kinase (TK), using the drug aminopterin which inhibits de novo purine and thymidylate synthesis; the TK synthesizes thymidylate; xanthine-guanine phosphoribosyltransferase (XGPRT), using the drug mycophenolic acid which inhibits de novo GMP synthesis; XGPRT synthesizes GMP from xanthine; and adenosine deaminase (ADA), using the drug 9-b-D-xylofuranosyl adenine (Xyl-A) which damages DNA; the ADA inactivates Xyl-A.

In addition to the recombinant DNA techniques described above for preparing a carboxyl-terminal core region of the gp41 ectodomain (C-terminus trimeric coiled coil motif of an HIV gp41 ectodomain), or C-terminal heptad repeat region of the ectodomain of another enveloped virus, such proteins may be synthesized using any number of well known techniques. For example, a carboxyl-terminal core region of the gp41 ectodomain may be prepared using the solid-phase synthetic technique initially described by Merrifield, in *J. Am. Chem. Soc.* 85:2149–2154 (1963). Other peptide synthesis techniques may be found in M. Bodanszky et al. *Peptide Synthesis*, John Wiley & Sons, 2d Ed. (1976) and other references readily available to skilled artisans. A summary of polypeptide synthesis techniques can be found in J. Stuart and J. D. Young. *Solid Phase Peptide Synthesis*, Pierce Chemical Company, Rockford, Ill., (1984). Peptides may also be synthesized by solution methods as described in *The Proteins*, Vol. II, 3d Ed., Neurath, H. et. al., Eds., p. 105–236, Academin Press, New York, N.Y. (I 1976). Appropriate protective groups for use in different peptide syntheses are described in the above-mentioned texts as well as in J. F. W. McOmie, *Protective Groups in Organic Chemistry,* Pelenu Press, New York, N.Y. (1973).

A carboxyl-terminal core region of the gp41 ectodomain (C-terminus trimeric coiled coil motif of an HIV gp41 ectodomain) or C-terminal heptad repeat region of the ectodomain of another enveloped virus, may also be prepared by chemical or enzymatic cleavage from larger portions of the corresponding protein.

Purified protein may be obtained by several methods. The protein or polypeptide of the present invention is preferably produced in purified form (preferably at least about 80%, more preferably 90%, pure) by conventional techniques. Typically, the protein or polypeptide of the present invention is secreted into the growth medium of recombinant host cells. Alternatively, the protein or polypeptide of the present invention is produced but not secreted into growth medium. In such cases, to isolate the protein, the host cell carrying a recombinant plasmid is propagated, lysed by sonication, heat, chemical treatment, and the homogenate is centrifuged to remove cell debris. The supernatant is then subjected to sequential ammonium sulfate precipitation. The fraction containing the polypeptide or protein of the present invention is subjected to gel filtration in an appropriately sized dextran or polyacrylamide column to separate the proteins. If necessary, the protein fraction may be further purified by HPLC.

Once a subject HIV gp41 trimer or C-terminal heptad repeat region of the ectodomain of another enveloped virus, has been isolated, it can be used to inhibit viral infection in a patient by vaccinating the patient. A patient may be administered an immunogenically effective amount of a subject stabilized HIV gp41 trimer comprising three gp41 monomers that form a trimeric coiled coil, in a prefusogenic conformation. Similarly, a patient may be administered an immunogenically effective amount of a C-terminal heptad repeat region of the ectodomain of another enveloped virus. By "immunogenically effective amount" it is meant an amount which is sufficient to induce protective humoral immunity in the subject. Such an amount is empirical and depends on factors such as the age, weight, gender, and diseased state of the subject. Generally speaking however, a polypeptide concentration in the range of from about 1 μM to about 100 mM may be administered.

Regardless of whether the polypeptides are used for vaccination, treatment or diagnosis, they can be administered orally, parenterally, subcutaneously, intravenously, intramuscularly, intraperitoneally, by intranasal instillation, by intracavitary or intravesical instillation, intraocularly, intraarterially, intralesionally, or by application to mucous membranes, such as, that of the nose, throat, and bronchial tubes. They may be administered alone or with pharmaceutically or physiologically acceptable carriers, excipients, or stabilizers, and can be in solid or liquid form such as, tablets, capsules, powders, solutions, suspensions, or emulsions.

The solid unit dosage forms can be of the conventional type. The solid form can be a capsule, such as an ordinary gelatin type containing the antibodies or binding portions thereof of the present invention and a carrier, for example, lubricants and inert fillers such as, lactose, sucrose, or cornstarch. In another embodiment, these compounds are tableted with conventional tablet bases such as lactose, sucrose, or cornstarch in combination with binders like acacia, cornstarch, or gelatin, disintegrating agents, such as cornstarch, potato starch, or alginic acid, and a lubricant, like stearic acid or magnesium stearate.

The polypeptide of the present invention may also be administered in injectable dosages by solution or suspension of these materials in a physiologically acceptable diluent with a pharmaceutical carrier. Such carriers include sterile liquids, such as water and oils, with or without the addition of a surfactant and other pharmaceutically and physiologically acceptable carrier, including adjuvants, excipients or stabilizers. Illustrative oils are those of petroleum, animal, vegetable, or synthetic origin, for example, peanut oil, soybean oil, or mineral oil. In general, water, saline, aqueous dextrose and related sugar solution, and glycols, such as propylene glycol or polyethylene glycol, are preferred liquid carriers, particularly for injectable solutions.

For use as aerosols, the polypeptide of the present invention in solution or suspension may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

Carrier molecules to which peptides of the invention are covalently linked (conjugated) are advantageously, non-toxic, pharmaceutically acceptable and of a size sufficient to produce an immune response in mammals. Examples of suitable carrier molecules include tetanus toxoid, keyhole limpet hemocyanin (KLH), and peptides corresponding to T cell epitopes (that is, T1 and T2) of the gp120 envelope glycoprotein that can substitute for non-AIDS virus-derived carrier molecules (Cease, Proc. Nat'l. Acad. Sci. (USA) 84:4249, 1987; Kennedy et al., J. Biol. Chem. 262:5769, 1987). Peptides can also be administered with a pharmaceutically acceptable adjuvant, for example, alum, or conjugated to other carrier molecules more immunogenic than tetanus toxoid. Linkage of a carrier molecule to a peptide of the invention can be direct or through a spacer molecule. Spacer molecules are, advantageously, non-toxic and well tolerated.

In addition, the HIV gp41 C-terminal trimer or C-terminal heptad repeat region of the ectodomain of another enveloped virus, may be used to generate antibodies against the trimer in its inactive conformation. The antibodies can be either polyclonal or monoclonal antibodies. These antibodies and binding portions thereof, recognize and bind to a C-terminus trimeric coiled coil motif of an HIV gp41 ectodomain or C-terminal heptad repeat region of the ectodomain of another enveloped virus. Monoclonal antibody production may be effected by techniques which are well-known in the art. Basically, the process involves first obtaining immune cells (lymphocytes) from the spleen of a mammal (e.g., mouse) which has been previously immunized with the antigen of interest either in vivo or in vitro. The antibody-secreting lymphocytes are then fused with (mouse) myeloma cells or transformed cells, which are capable of replicating indefinitely in cell culture, thereby producing an immortal, immunoglobulin-secreting cell line. The resulting fused cells, or hybridomas, are cultured, and the resulting colonies screened for the production of the desired monoclonal antibodies. Colonies producing such antibodies are cloned and grown either in vivo or in vitro to produce large quantities of antibody. A description of the theoretical basis and practical methodology of fusing such cells is set forth in Kohler and Milstein, Nature 256:495 (1975), which is hereby incorporated by reference.

Mammalian lymphocytes are immunized by in vivo immunization of the animal (e.g., a mouse) with the protein or polypeptide of the present invention. Such immunizations are repeated as necessary at intervals of up to several weeks to obtain a sufficient titer of antibodies. Following the last antigen boost, the animals are sacrificed and spleen cells removed.

Fusion with mammalian myeloma cells or other fusion partners capable of replicating indefinitely in cell culture is effected by standard and well-known techniques, for example, by using polyethylene glycol ("PEG") or other fusing agents (See Milstein and Kohler, Eur. J. Immunol. 6:511 (1976), which is hereby incorporated by reference). This immortal cell line, which is preferably murine, but may also be derived from cells of other mammalian species, including but not limited to rats and humans, is selected to be deficient in enzymes necessary for the utilization of certain nutrients, to be capable of rapid growth, and to have good fusion capability. Many such cell lines are known to those skilled in the art, and others are regularly described.

Procedures for raising polyclonal antibodies are also well known. Typically, such antibodies can be raised by administering the protein or polypeptide of the present invention subcutaneously to New Zealand white rabbits which have first been bled to obtain pre-immune serum. The antigens can be injected at a total volume of 100 ml per site at six different sites. Each injected material will contain adjuvants with or without pulverized acrylamide gel containing the protein or polypeptide after SDS-polyacrylamide gel electrophoresis. The rabbits are then bled two weeks after the first injection and periodically boosted with the same antigen three times every six weeks. A sample of serum is then collected 10 days after each boost. Polyclonal antibodies are then recovered from the serum by affinity chromatography using the corresponding antigen to capture the antibody. This and other procedures for raising polyclonal antibodies are disclosed in E. Harlow, et. al., editors, Antibodies: A Laboratory Manual (1988), which is hereby incorporated by reference.

Human monoclonal antibodies may be readily obtained in humanized mice. Such mice are commercially available from e.g., Abgenix, Inc., Fremont, Calif., and Medarex, Inc., Princeton, N.J. Human monoclonal antibodies may also be obtained using phage display libraries (Williamson, R. A., et al. 1998 *J Virol.* 72:9413–9418). Phage display libraries are commercially available from Cambridge Antibody Technology, Cambridge, Mass., and Biosyte, Md., and may be used in the present invention following the instructions of the manufacturer. Phage display libraries offer the possibility of obtaining panels of monoclonal antibodies to multiple putative targets in a very short time frame (one to three months).

In addition to utilizing whole antibodies, the processes of the present invention encompass use of binding portions of such antibodies. Such binding portions include Fab fragments, F(ab')2 fragments, and Fv fragments. These antibody fragments can be made by conventional procedures, such as proteolytic fragmentation procedures, as described in Goding, Monoclonal Antibodies: Principles and Practice, pp. 98–118, New York: Academic Press (1983), which is hereby incorporated by reference. The antibodies or binding portions thereof are particularly useful to inhibit HIV (or other enveloped virus) infectivity or for detecting the presence of HIV (or other enveloped virus) in a sample.

Thus, in accordance with the present invention, there is provided a method of inhibiting infectivity of an enveloped virus. The method comprises the steps of contacting the enveloped virus with a suitable amount of a subject antibody or binding region thereof under conditions effective to inhibit infectivity of the enveloped virus. The antibody or binding portion thereof may be administered to a host before or following exposure of the host to the enveloped virus.

In a preferred embodiment, there is provided a method of inhibiting HIV infectivity which comprises contacting HIV with a suitable amount of a subject antibody or binding region thereof under conditions effective to inhibit HIV infectivity. A subject antibody or binding portion thereof may be administered to a host before or following exposure of the host to an infective HIV strain.

In another aspect of the invention, there is provided a method of detecting HIV or other enveloped virus in a sample. The method comprises the steps of exposing a sample to an appropriate subject antibody or binding portion thereof, followed by identification of binding between the enveloped virus and the corresponding antibody or binding portion thereof. Thus, in order to detect HIV in a sample, the sample is exposed to a subject HIV antibody, hereinbefore described, or a binding portion thereof, and binding between HIV and the antibody or binding portion thereof, is identified. In order to detect SIV in a sample, the sample is exposed to a subject SIV antibody, hereinbefore described, or binding portion thereof, and binding between SIV and the antibody or binding portion thereof, is identified. In order to detect Mo-MLV in a sample, the sample is exposed to a subject Mo-MLV antibody, hereinbefore described, or binding portion thereof, and binding between Mo-MLV and the antibody or binding portion thereof, is identified. Likewise, in order to detect Ebola virus in a sample, the sample is exposed to a subject Ebola virus antibody, hereinbefore described, or binding portion thereof, and binding between Ebola virus and the antibody or binding portion thereof, is identified.

The present invention also provides a method for screening for drugs which can inhibit enveloped virus infection. In accordance with the method, a stabilized viral envelope protein trimer comprising a C-terminal heptad repeat region of the ectodomain in a prefusogenic conformation, is exposed to test compounds in order to identify compounds which bind thereto.

In a preferred embodiment, there is provided a method for screening for drugs which inhibit HIV infection. In accordance with the method, a gp41 trimer comprising three gp4 monomers that form a trimeric coiled coil in a prefusogenic conformation, is exposed to test compounds in order to identify those compounds which bind to the gp41 trimer. In particular, the method identifies compounds where gp41, which is bound to the compound, binds less effectively to gp120 than gp41 not bound to the compound.

Although the invention has been described in detail for the purpose of illustration, it is understood that such detail is solely for that purpose, and variations can be made therein by those skilled in the art without departing from the spirit and scope of the invention. The invention is further illustrated by the following examples which are not intended in any way to limit the scope of the invention.

EXAMPLE 1

Construction of a chimera of gp41 and GCN4-pII.

Figure 2:
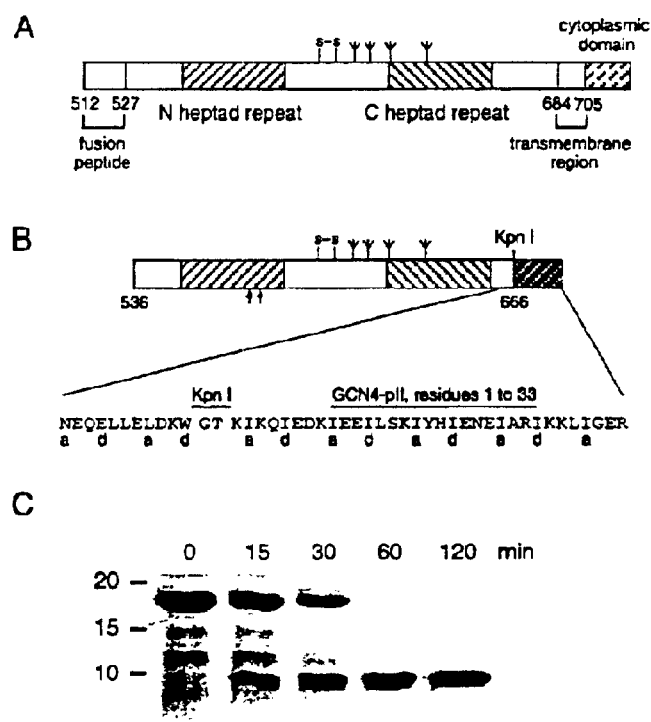
FIG. 2A is a schematic view of gp41. The locations of the $NH_2$- and COOH-terminal hydrophobic heptad repeats are indicated. The disulfide bond and four potential N-glycosylation sites are depicted.
FIG. 2B schematically depicts a chimera of gp41 (residues 536 to 666) and the GCN4-pII peptide (14). The amino acid sequence of the COOH-terminal extension of gp41 is shown in an expanded view (SEQ ID NO:1). Residues in the a and d positions of gp41 residues, and GCN4-pII in heptad register, are indicated. A continuous helix is assumed between the gp41 coiled coil and GCN4-pII. The locations of serine substitutions for $Ile^{573}$ and $Leu^{576}$ in the NH2-terminal heptad-repeat region are indicated by arrows.
FIG. 2C is a photographic reproduction of an Coomassie blue stained SDS-Polyacrylamide gel run with the gp41/GCN4-pII chimera, digested with trypsin for the times indicated. The sizes of protein molecular weight markers (in kDa) are indicated at the left.

Formation of native envelope glycoprotein trimers on infectious virions is thought to be mediated by a sequence within the gp41 ectodomain other than the $NH_2$-terminal coiled-coil motif (FIG. 2A) (10). Trimerization therefore may therefore depend on a hydrophobic heptad repeat located in the COOH-terminal region of the protein. Earlier studies indicate the native structure of the gp120/gp41 complex is labile (11), and is transformed by receptor binding into an energetically more stable fusogenic conformation (5–7). Experiments were thus designed in order to test whether stabilizing this COOH-terminal coiled-coil motif could capture the gp41 molecule in the native metastable fold. Accordingly, the gp41 ectodomain, lacking the $NH_2$-terminal fusion peptide was engineered, by placing a soluble trimeric isoleucine zipper (GCN4-pII) in heptad register to the COOH terminus of the coiled-coil segment replacing the 17-residue region prior to the transmembrane anchor (FIG. 2B)

The genes of gp41 (residues 536 to 666, numbered according to their position in gp160 the HXB2 HIV-1 strain) and GCN4-pII (14) were subcloned into the expression vector pTMHa [J. P. Staley and P. S. Kim, *Protein Science* 3, 1822 (1994)] to produce plasmid pRgp41pII (FIG. 2B). $Met^{629}$ in the pRgp41pII construct was mutated to leucine by single-stranded mutagenesis [(T. A. Kunkel, J. D. Roberts, R. A. Zakour, *Methods Enzymol.* 154, 367 (1987)] An expression vector (pC45pII) encoding the C45-pII peptide was derived from pRgp41pII by PCR amplification followed by subcloning into pTMHa. The KpnI site in pC45pII was replaced by the coding sequence for the residues Ala-Ser. Plasmid pC45 was derived from pC45pII. Plasmid pC52 was derived from pC45pII by the insertion of the appropriate DNA sequences encoding the residues Leu-Trp-Asn-Trp-Phe-Asn-Ile (SEQ ID NO:7) in place of GCN4-pII. Plasmid pC29p was derived from pC45pII. Single letter abbreviations for amino acid residues are as follows: A, Ala; C, Cys; D, Asp; E, Glu; F, Phe; G, Gly; H, His; I, Ile; K, Lys; L, Leu, M, Met; N, Asn; P, Pro; Q, Gln; R, Arg; S, Ser; T, Thr; V, Val; W, Trp; and Y, Tyr.

In addition, Ile$^{573}$ and Leu$^{576}$ were mutated in this chimera molecule to polar serine residues in order to destabilize the NH$_2$-terminal coiled coil because it forms the centre of fusion-active gp41 (6, 12). The resulting chimera protein was designated rgp41-pII.

The rgp41-pII protein was produced by bacterial expression, purified by reverse-phase high-performance liquid chromatography, and refolded in vitro. Proteins were expressed in the *E. coli* strain BL21(DE3)/pLysS (Novagen). The chimeric proteins and peptides were purified essentially as described for the N36-pl peptide [W. Shu, H. Ji, M. Lu, *Biochemistry* 38, 5378 (1999)]. Cys-containing proteins were subjected to air oxidation in 6 M guanidine hydrochloride (GdmCl), and 100 mM tris-HCl (pH 8.6) to permit disulfide bond formation prior to cyanogen bromide treatment. Purified rgp41-pII solubilized in 6 M GdmCl and 50 mM tris-HCl (pH 8.0) was refolded by dilution into 50 mM tris-HCl (pH 8.0). Identity of the peptides was confirmed by mass spectrometry (Perceptive Biosystems Voyager Elite), and all molecular masses were found to be within 2 daltons of the expected mass.

Figure 3:
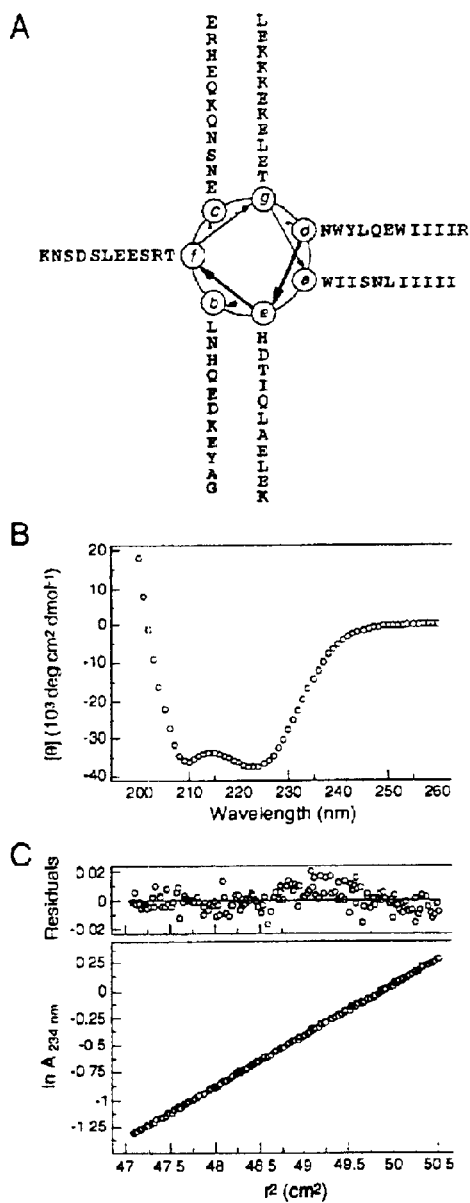
FIG. 3A shows the helical wheel projection of C45-pII (SEQ ID NO:2). View is from the $NH_2$ terminus. The amino acid sequence of C45 (residues 624 to 668) is shown in red. The residues in black are from GCN4-pII. The residue in blue corresponds to a conservative leucine substitution for $Met^{629}$, made to facilitate protein production.
FIG. 3B shows a CD spectrum of a 10 μM solution of C45-pII at 0° C. in PBS (pH 7.0).
FIG. 3C shows sedimentation equilibrium data (17,000 rpm) of C45-pII at ~10 μM at 4° C. in PBS (pH 7.0). The natural logarithm of the absorbance at 234 nm is plotted against the square of the radial position. The random distributions of the residuals indicate that the data fit well to an ideal single-species model.

The rgp41-pII protein forms an insoluble aggregate under physiological conditions. Protease treatment with trypsin resulted in a soluble peptide fragment that extends from Ser$^{618}$ to the COOH-terminal end of the recgp41-pII construct, including the gp41 segment (residues 618 to 666) on the NH$_2$ terminus and the entire GCN4 coiled coil on the COOH terminus (FIG. 2C). To facilitate further studies, a molecule denoted C45-pII, was constructed in which the C45 segment (residues 624 to 668) of gp41 is fused in frame to GCN4-pII (FIG. 3A). The circular dichroism (CD) spectrum of C45-pII demonstrates that the peptide is fully helical in solution (FIG. 3B).

EXAMPLE 2

Alpha-helical structure of the chimera.

In an attempt to define a smaller subdomain for high-resolution crystallographic studies, C45-pII was subjected to proteolysis by proteinase K. Trypsin (Worthington) or proteinase K (Boehringer Mannheim) digestions were performed with 1 mg/ml protein and 0.01 mg/ml at room temperature in 50 mM tris-HCl (pH 8.0) and were quenched with 4 mM phenylmethylsulphonyl fluoride (Sigma). The proteolytic fragments were separated and purified by reverse-phase high-performance liquid chromatography. The purified fragments were characterized by NH$_2$-terminal sequencing and mass spectrometry.

The digestion yields a slightly shorter 56-residue fragment corresponding to residues 640 to 668 of gp41 and residues 1 to 27 of GCN4-pII. This fragment, designated C29-p, represents a 16-residue truncation from the NH$_2$ terminus and a 6-residue truncation from the COOH terminus. Like the longer C45-pII peptide, C29-p forms a discrete trimer with 100% helix content.

CD spectra were acquired on an Aviv 62DS circular dichroism spectrometer. Measurements of $[\theta]_{222}$ were made at 0° C. in 50 mM sodium phosphate (pH 7.0) and 150 mM NaCl. A $[\theta]_{222}$ value of −33,000 degrees cm$^2$ dmol$^{-1}$ was taken to correspond to 100% helix [Y. H. Chen, J. T. Yang, K. H. Chau, *Biochemistry* 13, 3350 (1974)]. Thermal melts were performed in the same buffer by measuring $[\theta]_{222}$ as a function of temperature [C. R. Cantor and P. R. Schimmel, *Biophysical Chemistry* (Freeman, N.Y., 1980), vol. 3, p. 1132]. Peptide concentrations were determined spectrophotometrically in 6 M GdmCl [H. Edelhoch, *Biochemistry* 6, 1948 (1967)].

Sedimentation equilibrium measurements were carried out on a Beckman XL-A analytical ultracentrifuge equipped with an An-60 Ti rotor. All experiments were performed in 50 mM sodium phosphate (pH 7.0) and 150 mM NaCl at 4° C. and peptide concentrations of 10, 30, and 100 μM. Data for C45-pII and C29-p showed no systematic dependence of molecular weight on concentration. At concentrations below 25 μM, the molecular weights of the C52 and Q652L peptides varied systematically between monomer and trimer values. Data for N656L were not fit to a single-species model [K. E. Van Holde, *The Proteins*, H. Neurath and R. L. Hill, Eds. (Academic Press, San Francisco, 1975), vol. 1, pp. 225] and showed systematic dependence of molecular weight on concentration. The molecular weights derived from the data sets (followed by expected molecular weight for a trimer) and [the rotor speeds in thousand revolutions per minute at which data were collected] are as follows: C45-pII -30,342 (28,463) [17, 20]; C29p-21,748 (20,150) [19, 22]; C52-18,028 (19,464) [19, 22]; Q652L-17,708 (19,419) [19, 22]. Sedimentation equilibrium experiments indicate that the C45-pII peptide sediments as a trimeric species (FIG. 3C) (17). Thus, the chimera of the gp41 heptad repeat and isoleucine zipper can form a protease-resistant, three-helix structure.

EXAMPLE 3

Folding of the C52 coiled-coil domain.

Figure 4:
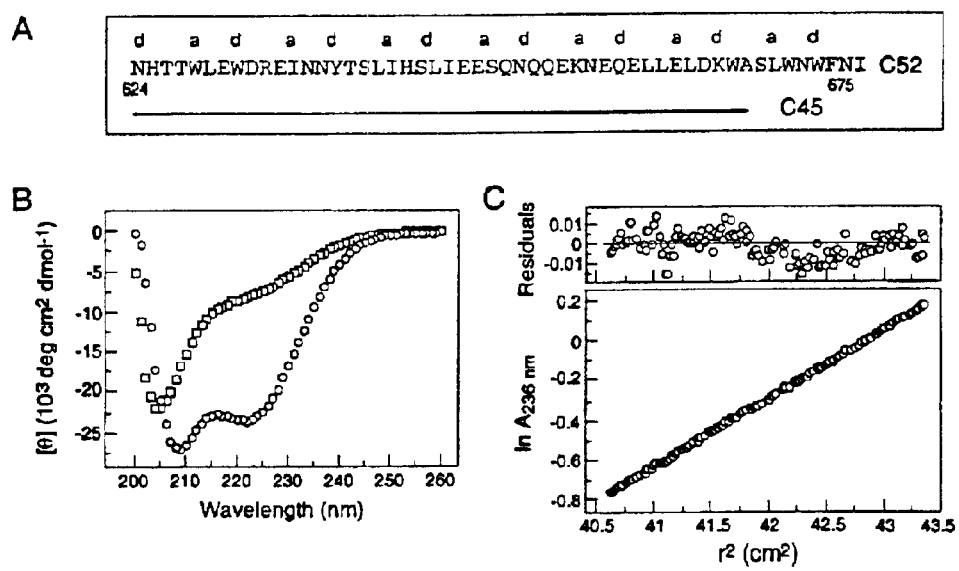
FIG. 4A shows the amino acid sequence of C52 with the a and d positions of the heptad repeat indicated above the sequence (SEQ ID NO:3). The sequence of the C45 peptide is also indicated.
FIG. 4B shows the CD spectra of C52 (circles) and C45 (squares) at 0° C. in PBS (pH 7.0) at 100 μM peptide concentration.
FIG. 4C shows sedimentation equilibrium data (19,000 rpm) of C52 at ~30 μM at 4° C. in PBS (pH 7.0). The natural logarithm of the absorbance at 236 nm is plotted against the square of the radial position. The random distributions of the residuals indicate that the data fit well to an ideal single-species model.

In contrast to the C45-pII chimera, the isolated C45 peptide (residues 624 to 669 of gp41) displays little secondary structure, as judged by CD spectroscopy (15). To investigate the possibility that the heptad-repeat motif might be stabilized in the context of the longer coiled coil, a 52-residue peptide, designated C52, that contains the entire C45 region plus 7 residues on the COOH terminus (FIG. 4A), was studied. The C52 peptide is ~70% helical and exhibits a reversible thermal unfolding transition at 100 μM peptide concentration in neutral pH phosphate-buffered saline (PBS) at 0° C. (FIG. 4B, C). Because the mutant envelope glycoprotein exhibits substantial cell-surface expression, gp160 precursor processing, CD4 binding, gp120/gp41 association, and soluble CD4-induced shedding (7), the fusion-defective Asn$^{656}$ to Leu mutation is unlikely to alter structural features sufficiently to disrupt the native gp120/gp41 complex.

Sedimentation equilibrium measurements indicate that the C52 peptide is a trimer between 30 and 100 μM (FIG. 4D). The molecular weight of the C52 peptide systematically decreases at concentrations below 25 μM (presumably because of dissociation in the low micromolar concentration range). Thus, the C52 peptide forms a labile three-stranded coiled coil in isolation. The invariant Trp$^{670}$ and Phe$^{673}$ residues in positions a and d of the C52 peptide may contribute to the folding free energy of the coiled-coil trimer.

EXAMPLE 4

Model for the native conformation of gp41.

Figure 5:
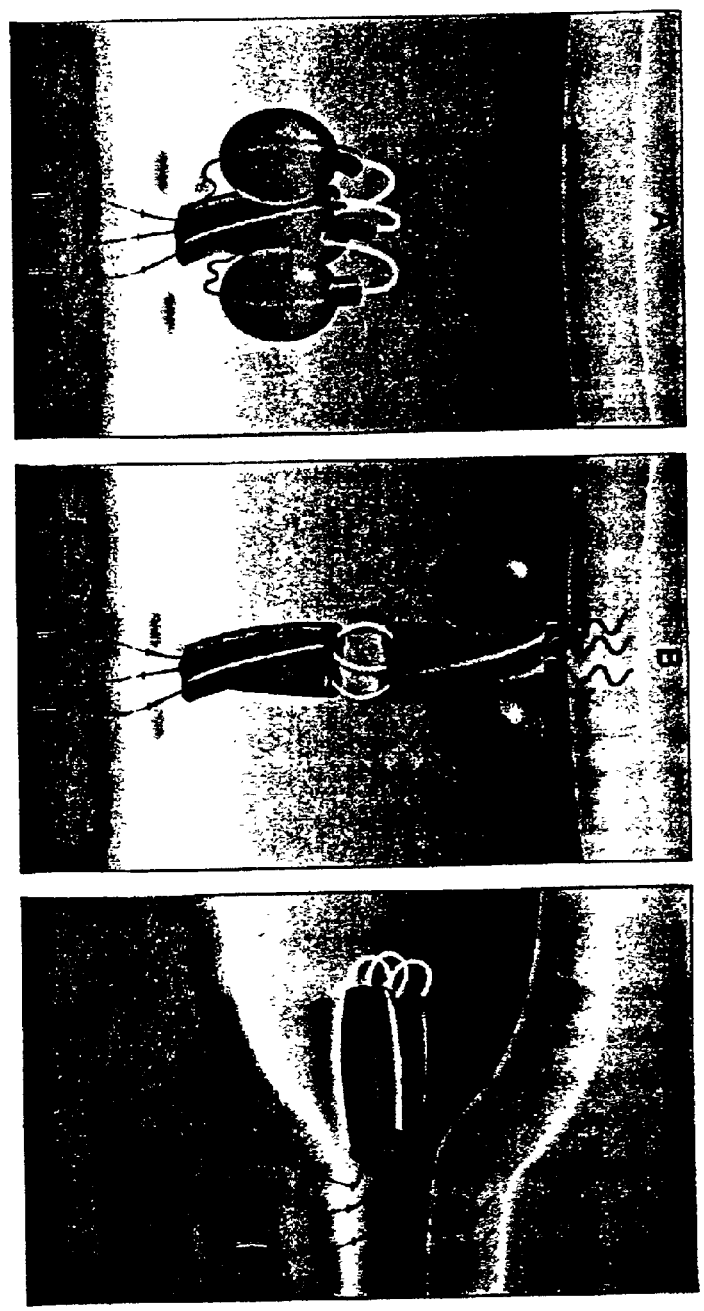
FIG. 5A schematically depicts the trimeric gp120/gp41 complex in the native state. The COOH-terminal coiled coil (red) in gp41 is present, while the $NH_2$-terminal heptad-repeat region (blue) and fusion peptide (brown) are involved in interaction with the gp120 subunit (green balls).
FIG. 5B schematically depicts the trimeric gp120/gp41 complex following binding of gp120 to cell-surface receptors, where gp41 undergoes a conformational change to the transient prehairpin intermediate, and the $NH_2$-terminal coiled coil is formed. As a result, the fusion peptide region inserts into the cellular membrane at the top of the molecule.
FIG. 5C shows the trimeric gp120/gp41 in the fusogenic state, where the COOH-terminal helices are packed in an antiparallel manner against the $NH_2$-terminal coiled coil, advancing two lipid bilayers toward intimate approximation and fusion. Formation of the stable trimer-of-hairpins structure is likely to provide a ready source of the activation energy needed for this membrane apposition process.

The finding that the C52 peptide can fold into an α-helical trimer leads to a proposal of a model for the native conformation of gp41 (see FIG. 5). The COOH-terminal regions of the three gp41 chains form a parallel trimeric coiled coil that is ~9 residues from the viral membrane end of the molecule. The NH$_2$-terminal heptad-repeat regions make contacts with the gp120 subunits, and are thus held in an non-coiled-coil conformation (FIG. 5A). The gp120 chains may also contribute to the native structure but primarily form three membrane distal globular domains containing the receptor-binding sites. This native conformation is presumably stabilized by interactions between gp120 and gp41 as well as burial of the apolar fusion peptide in the interior of the gp120/gp41 complex. According to present theories (3, 5), binding of gp120 to CD4 and a chemokine receptor alters the intersubunit interactions and thus initiates cooperative folding of the gp41 $NH_2$-terminal coiled coil, leading to the exposure of the fusion peptide and its insertion into the target membrane. As a result, a transient gp41 intermediate exists as a prehairpin molecule simultaneously in both the viral and cellular membranes (FIG. 5B) (16). At the COOH-terminal end the coiled-coil trimer then refolds into three helices, allowing them to pack against the $NH_2$-terminal trimeric coiled coil in an inverted orientation (FIG. 5C). Thus, the temporal disassembly of the native coiled-coil domain for generating the fusogenic hairpin structure serves as a flip-flop mechanism for activating the membrane fusion potential of gp41.

EXAMPLE 5

Correlation with genetic studies.

Figure 6:
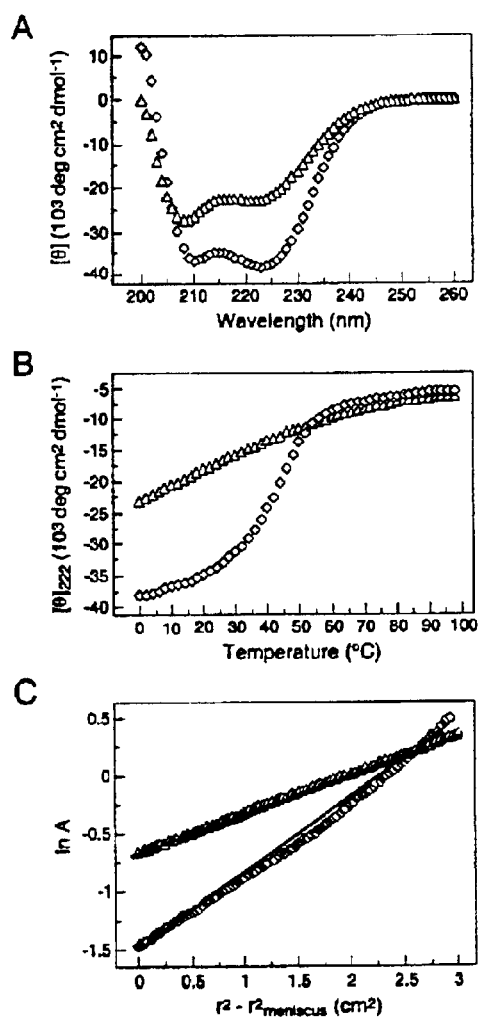
FIG. 6A are the CD spectra showing folding of the C52 mutant peptides Q652L (triangles) and N656L (rhombi) at 0° C. in PBS (pH 7.0) at 100 μM peptide concentration.
FIG. 6B are thermal melts of Q652L (triangles) and N656L (rhombi) in PBS (pH 7.0) at 100 μM peptide concentration.
FIG. 6C shows sedimentation equilibrium data (19,000 rpm) for Q652L (triangles) at ~100 μM and N656L (rhombi) at ~30 μM collected at 4° C. in PBS (pH 7.0). For an ideal, single-species system, the plot of the natural logarithm of the absorbance against the square of the radial position is linear, with the slope proportional the molecular weight of the molecule (18). In a multi-species system, however, the plot becomes curved upward (18).

In the trimer-of-hairpins structure of fusion-active gp41, the conserved $Gln^{652}$ and $Asn^{656}$ residues at the d and a positions of the outer helix respectively are packed into a hydrophobic groove on the surface of the $NH_2$-terminal coiled coil (6). Whereas the $Asn^{656}$ to Leu mutation abolishes membrane fusion, the $Gln^{652}$ to Leu mutation increases HIV-1 infectivity (17). To define the basis for these in vivo phenotypes, the role of $Gln^{652}$ and $Asn^{656}$ on coiled-coil interactions was investigated by characterizing variants of the C52 peptide: Q652L and N656L (SEQ ID NO:9). The Q652L peptide was derived form the C52 peptide (residues 624–675) by substituting a leucine for glutamine at position 652. The N652L peptide was also derived from the C52 peptide by substituting a leucine for asparagine at position 656. Both peptides were made by single stranded mutagenesis using the method described in Kunkel, T. A., et al., *Methods Enzymol.* 154, 367 (1987), and produced by bacterial expression. On the basis of CD measurements at 100 μM peptide concentration in PBS (pH 7.0) at 0° C., Q652L is ~70% helical and N656L (SEQ ID NO:9) is fully helical (FIG. 6A). Under these conditions, Q652L displays a broad thermal unfolding transitions and N656L melts cooperatively with a $T_m$ of 43° C.(FIG. 6B). The Q652L peptide sediments as a trimer at concentrations between 30 and 100 μM (FIG. 6C). The N656L peptide does not sediment as a unique oligomeric species; its apparent molecular weight changes significantly with peptide concentration (FIG. 6C). The $Gln^{652}$ to Leu substitution therefore essentially exerts no effects on formation of C52 trimers, while the $Asn^{656}$ to Leu substitution imparts strong helical character at the expense of structural uniqueness.

It has been previously shown that that leucine is favored (~0.8 kcal $mol^{-1}$) over $Gln^{652}$ at the fusion-active hairpin structure (18). If the stability of the trimeric C52 coiled coil, hence the native gp120/gp41 structure, is assumed to be unaffected by the $Gln^{652}$ to Leu mutation, then it follows that its energetic preference for the fusogenic conformation provides a higher-than-wild-type driving force for membrane fusion. Therefore, increasing the stability of the native state by the $Asn^{656}$ to Leu mutation prevents the conformational change and inhibit membrane fusion activity. Thus, the labile nature of the COOH-terminal three-stranded coiled coil of gp41 is likely important in facilitating its conformational activation required for membrane fusion.

EXAMPLE 6

Implications for gp41 function.

Results obtained in the preceding examples indicate that extensive rearrangement and refolding of α-helical coiled coils in the gp41 molecule is the basis of the flip-flop molecular model for triggering formation of the fusogenic conformation (FIGS. 5A–5B). These changes in conformation indicate that a two-stage reaction mechanism is responsible for initiating membrane fusion. In the first, the fusion-peptide region is extruded from the native gp120/gp41 core to the tip of the newly created $NH_2$-terminal trimeric coiled coil, thus allowing its insertion into the bilayer of the target membrane (FIG. 5B) (19). In the second, the COOH-terminal coiled-coil trimer dissociates, and the resulting three helices relocate with reversal of chain direction and pack against the outer surface of the $NH_2$-terminal coiled coil. These two structural changes produce a thermodynamically stable, fusogenic hairpin structure (FIG. 5C). Hairpin formation is thought to bring the viral and cellular membranes together at the fusion site by juxtaposition of the membrane anchor and the fusion peptide (7), but the detailed mechanism by which membrane apposition leads to the actual coalescence of the two bilayers is unknown. Because the trimer-of-hairpins structure is a common feature of diverse viral membrane fusion proteins (28), this type of activation and refolding could be a general mechanism of viral membrane fusion.

The model of gp41 activation based on results from this study is fully consistent with mutagenesis studies. First, site-directed point mutations in the $NH_2$-terminal coiled-coil sequence abolish membrane fusion but have little effect on the oligomerization of the native gp120/gp41 complex (10, 17). Second, the native gp41 structure is thought to be trapped in a labile conformation through gp120-gp41 interactions (4). Consistent with metastable folding of gp41 is the observation that the fusion-enhancement $Gln^{652}$ to Leu mutation helps tip the balance between the labile native and most stable fusogenic states (18). In contrast, the leucine replacement for the buried $Asn^{656}$ residue characterized here may fail to produce a sufficient free energy difference between the native and fusogenic folds, thus preventing gp41 activation. Hence, two types of helix-helix interactions in gp41 enable structural rearrangements to take place in a concerted fashion. Third, mutations in gp41 that abrogate gp120 association map to residues in the $NH_2$-terminal half of the molecule (17, 21). The gp120-gp41 interaction is thought to be responsible for poising the native conformation, with gp120 shedding allowing formation of the trimer-of-hairpins structure upon receptor binding (12). These studies demonstrate directly that the $NH_2$-terminal heptad-repeat region of gp41 is indeed an important part of the triggering mechanism for fusion activation.

EXAMPLE 7

Construction of a chimera of C52 and GCN4-pII.

As demonstrated in Example 3, a 52-residue peptide (referred to as C52) derived from the COOH-terminal region of the gp41 ectodomain forms a labile, trimeric coiled coil (FIG. 1) (38). This finding has led to the hypothesis that this coiled-coil domain within the native envelope glycoprotein complex brings three gp41 molecules into close proximity in order to facilitate their conformational activation during HIV-1 infection. Thus, the C52 coiled coil appears to be exposed on the surface of the infectious virus, raising the possibility that it is a vulnerable target for humoral defense and thus a superior immunogen for effective antibody induction.

Figure 7:
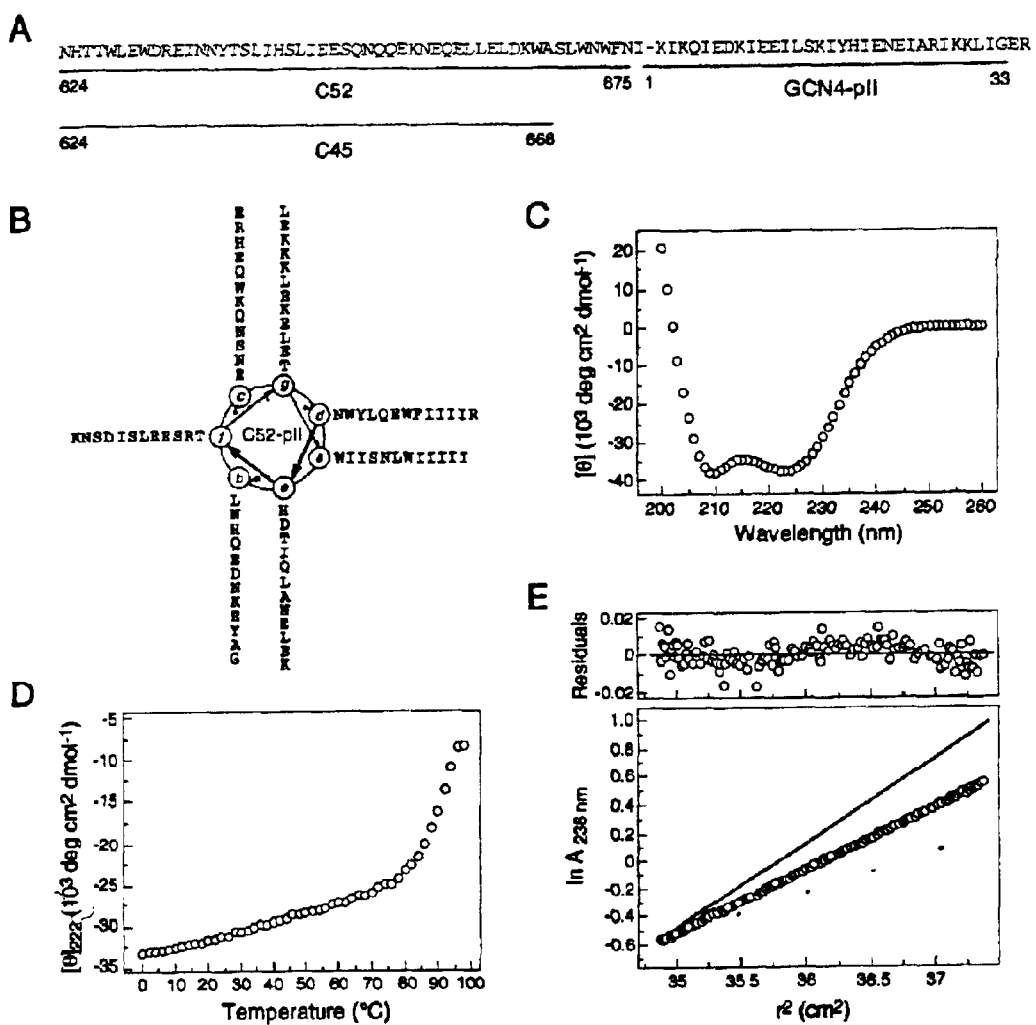
FIG. 7A illustrates the chimera of the C52 peptide (residues 624 to 675) and an isoleucine-zipper trimer (GCN4-pII) (SEQ ED NO:4). Met629 in the C52-pII molecule was mutated to leucine to facilitate protein production. The location of the C45 segment (residues 624 to 668) is indicated. The gp41 residues are numbered according to their position in gp160 of the HXB2 HIV-1 strain.
FIG. 7B is a helical wheel representation of C52-pII (SEQ ID NO:4). The sequence of C52 is shown in red, while the residues in black are from GCN4-pII. A continuous helix is assumed between the C52 coiled coil and GCN4-pII. View is from the NH2 terminus.
FIG. 7C is a CD spectrum of a 5 mM solution of C52-pII at 4° C. in PBS (pH 7.0).
FIG. 7D is a thermal melt of C52-pII monitored by CD at 222 nm in the presence of 4 M GdmCl, a denaturant.
FIG. 7E shows sedimentation equilibrium data (16,000 rpm) of C52-pII at ~50 mM at 20° C. in PBS (pH 7.0). The natural logarithm of the absorbance at 254 nm is plotted against the square of the radial position. The random distributions of the residuals indicate that the data fit well to an ideal single-species model. The calculated data for dimeric and tetrameric models are indicated by dashed and solid lines, respectively.

To stabilize this coiled-coil trimer for immunogenicity studies, a peptide was constructed in which the 52 residues of the C52 peptide were fused in heptad repeat to the 333 residues of a trimeric GCN4 coiled coil (GCN4-pII) (FIG. 7A). An expression vector (pC52pII) encoding the C52-pII peptide was derived from pC45-pII (38) by the insertion of the appropriate DNA sequences encoding the residues LeuTrpAsnTrpPheAsnIle between the COOH terminus of C52 and the $NH_2$ terminus of GCN4-pII. Proteins were expressed in the *E. coli* strain BL21 (DE3)/pLysS (Novagen) and purified essentially as described for the N36-pl peptide [Shu, W., Ji, H., Lu, M., *Biochemistry* 38, 5378 (1999)]. The expected molecular weights of all concentrations were determined spectrophotometrically in 6M GdmCl [Edelhoch, H., *Biochemistry* 6, 1948 (1967)].

The resulting chimera, C52-pII, was expressed as a recombinant protein in *E. coli* and purified by reverse-phase high-performance liquid chromatography. CD spectra were acquired on an Aviv 62DS circular dichroism spectrometer. Measurements of $[\theta]_{222}$ were made at 5 μM peptide concentration and 4° C. in 50 mM sodium phosphate (pH 7.0) and 150 mM NaCl. A $[\theta]_{222}$ value of −33,000 degrees $cm^2$ $dmol^{-1}$ was taken to correspond to 100% helix [Y. H. Chen, J. T. Yang, K. H. Chau, *Biochemistry* 13, 3350 (1974)]. Thermal melts were performed in the same buffer and also with the addition of 4 M GdmCl to facilitate unfolding by measuring $[\theta]_{222}$ as a function of temperature [C. R. Cantor and P. R. Schimmel, *Biophysical Chemistry* (Freeman, N.Y., 1980), vol. 3, p. 132].

On the basis of circular dichroism measurements, C52-pII is fully helical (FIG. 7C) and has a thermal stability that exceeds 100° C. In the presence of the denaturant guanidinium hydrochloride (GdmCl) at 4 M concentration, C52-pII melts cooperatively with an apparent melting temperature of 89° C. (FIG. 7D).

Sedimentation equilibrium experiments were performed on a Beckman XL-A analytical ultracentrifuge equipped with an An-60 Ti rotor. C52-pII solutions were dialyzed overnight against 50 mM sodium phosphate (pH 7.0) and 150 mM NaCl, loaded at initial concentrations of 5, 15, and 50 μM, and analyzed at 16,000 and 19,000 rpm at 20° C. Data were acquired at two wavelengths per rotor speed and processed simultaneously with a nonlinear least squares fitting routine [M. L. Johnson, J. J. Correia, D. A. Yphantis, H. R. Halvoson, *Biophys. J.* 36, 575 (1981)]. Solvent density and protein partial specific volume were calculated according to solvent and protein composition, respectively [T. M. Laue, B. D. Shah, T. M. Ridgeway, S. L. Pelletier, in *Analytical Ultracentrifugation in Biochemistry and Polymer Science*, S. E. Harding, A. J. Rowe, J. C. Horton, Eds. (Royal Society of Chemistry, Cambridge, 1992), pp. 90–125]. The data fit well to a model for an ideal trimer, with no systematic deviation of the residuals. The observed molecular weight is 32,100 daltons, compared to an expected value of 31,400 daltons for a trimer.

Sedimentation equilibrium measurements indicate that the C52-pII peptide is a discrete trimer and exhibits no systematic deviation from trimer molecular weight between 5 and 50 μM (FIG. 7E). Thus, C52-pII forms a well-structured and extremely stable, three-stranded coiled coil.

EXAMPLE 8

Eliciting neutralizing antibodies.

To explore the immunogenicity of the COOH-terminal coiled-coil region of gp41, the C52-pII, C52, and C45-pII model peptides were used to immunize rabbits. To generate antisera, two rabbits each were immunized with the peptide C52-pII, C52 or C45-pII. The primary immunization was performed with a dose of 500 μg of peptide immunogen emulsified (1:1 mixture) in complete Freund's adjuvant. The animals were subsequently challenged with 250, 250, 125, and 125 μg of the immunogen with incomplete Freund's adjuvant for each of four booster immunizations at 3-week intervals. Sera collected 2 weeks after the third booster inoculation were used for the studies described here. Rabbit polyclonal antibodies (total IgG) were purified from serum on a protein A-Sepharose column (Amersham Pharmacia Biotech). Total IgG concentrations were determined by absorbance at 280 nm (1 optical density=0.8 mg/ml). The rabbit antibodies were generated by Covance Research Products, Inc. (Denver, Pa.).

The C52 and C45-pII molecules were chosen as controls because the former is predominantly unfolded under physiological conditions and the latter lacks seven highly conserved hydrophobic amino acids at the COOH-terminus of the gp41 coiled-coil segment, relative to C52-pII (38).

The purified polyclonal antibodies from the rabbit sera were tested for neutralization of a panel of isolates of HIV-1. Neutralization against primary isolates was assessed using PHA-activated PBMC (phytohemagglutinin activated peripheral blood monocytes) as indicator cells and determination of p24 antigen production as the endpoint. PBMC were isolated and stimulated with PHA (5 μg/ml) for 48 hrs followed by PHA and IL-2 (40 U/ml) for 72 hrs in RPMI 1640 containing 10% heat-inactivated FBS, 100 U/ml penicillin, 100 μg/ml streptomycin and 2 mM L-glutamine. The antibodies were diluted and 50 μl per well were pipetted in round bottom microtiter plates, after which an equal volume containing 100 TCID50 of primary isolate stock was added. The antibody-virus mixture was incubated for 1 hr at 37° C. Next, 100 μl PHA-activated PBMC ($5 \times 10^5$/ml) were added to each well. The calculated neutralization titers refer to the antibody (Ab) concentration present during this incubation step. After an overnight incubation, the cells were washed two times with tissue culture medium (RPMI). On day 4, 100 μl of the medium was replaced with fresh tissue culture medium. On day 7, the cultures were collected and treated with 1% v/v Empigen (Calbiochem). Triplicate samples were then tested for p24 content using ELISA (Moore, J. P., et al., *Science* 250, 1139–1142). In brief, sheep anti-gp120 Ab D7320 (Aalto Bioreagents) was coated overnight on 96-well polystyrene EIA plates (Costar) in 100 mM NaHCO3 pH 8.5. The plates were washed in PBS and p24 was captured from serial dilutions of the HIV-1 containing samples in PBS/0.1% Empigen. After a 3 hr incubation, unbound p24 was washed away and bound p24 was detected with alkaline phosphatase-labeled Ab BC1071 (International Enzymes) diluted 1:3,000 in PBS containing 20% sheep serum and 2% NFDM. After a 1h incubation, the plates were washed and developed with an AMPAK kit (Dako Diagnostics) as recommended by the manufacturer. Production of p24 antigen in the Ab-containing cultures was compared to p24 production in cultures without Ab run in the same assay and the Ab concentrations resulting in a 50% and 90% reduction in p24 content were determined.

Results reported herein indicate that stable, trimeric versions of the gp41 COOH-terminal heptad-repeat region as a component of combination vaccines against HIV-1 infection. (Table 1) C52-pII(B) is able to elicit antibodies capable of efficient neutralization of primary HIV-1 isolates. See Table 1.

TABLE 1

Neutralization of HIV-1 primary isolates by the antiserum C85-pII(B)

| HIV-1 | EC50IgG (µg/ml) | | | | | | |
|---|---|---|---|---|---|---|---|
| | NL4-3 | JRFL | 92US657 | 2076c1.3 | HC4 | DH123 | SF162 |
| C52-pII(B) | 214.03 | 135.08 | 105.39 | >500 | >500 | 215.43 | 135.42 |
| 2F5 | 15.18 | 4.37 | 57.83 | 38.13 | 34.18 | — | — |
| CD4-IgG2 | 0.21 | 0.51 | >10 | >10 | >10 | 5.18 | <0.062 |

Given the similarity in structure between C52-pII and C45-pII, and the identity in the gp41 portion between C52-pII and C52, it appears that a trimeric coiled-coil segment formed by the sequence LWNWFNI ((SEQ ID NO:7); amino acids 669 to 675 of gp41) is involved in raising neutralizing antibodies. $Trp^{670}$ and $Trp^{672}$ are completely conserved in 213 fully sequenced M group HIV-1 strains, while there is only a single conservative methionine substitution for $Ile^{675}$. In addition, $Ile^{669}$ and $Phe^{673}$ occur in 205 and 204 of the 213 sequences respectively, with only a single nonconservative change present at each position. Even two more variable positions (671 and 674) are occupied by single polar and negatively charged residues in more than 75 and 60% of the sequences respectively; all the remaining sequences at each position possess conservative changes. It appears therefore, that there is selective pressure on the a and d positions to maintain trimeric coiled-coil interactions, as well as pressure on the outside heptad positions to preserve particular types of amino acid character. These conserved sequence and structural elements likely underlie the ability of $C^{52}$-pII to elicit broadly reactive neutralizing antibodies, thus making it an attractive candidate for vaccine efforts.

Immediately $NH_2$-terminal to the sequence LWNWFNI (SEQ ID NO:7) is an epitope (the linear sequence ELDKWA; SEQ ID NO:6) recognized by the human antibody 2F5 isolated from an HIV-1-infected donor (S1). Because the immunizing C52-pII peptide was able to abrogate the fusion inhibition activity of the neutralizing antibodies, whereas C52 and C45-pII (both containing ELDKWA) were not (FIG. 8), it is likely that the discontinuous neutralization determinant defined in this study is different from the continuous 2F5 epitope. Consistent with this notion is the observation that C85-pIIB serum and 2F5 represent different specificities in neutralizing seven primary clinical isolates tested (Table 1). Thus, the conserved, conformation-specific epitope in the C52-pII 'tailor-made' molecule appears to produce more effective antibody responses than a natural HIV-1 infection. cl REFERENCES 1. Reviewed in P. A. Luciw, in *Fields Virology*, B. N. Fields, D. M. Knipe, P. M. Howley, R. M. Chanock, J. L. Melinick, T. P. Monath, B. Roizman, S. E. Straus, Eds. (Lippincott-Raven Publishers, Philadelphia, 1996), pp. 1881–1952; E. Q. Freed and M. A. Martin, *J. Biol. Chem.* 270, 23883 (1995).
2. P. D. Kwong, R. Wyatt, J. Robinson, R. W. Sweet, J. Sodroski, W. A. Hendrickson, *Nature* 393,648 (1998); C. D. Rizzuto, R. Wyatt, N. Hernandez-Ramos, Y. Sun, P. D. Kwong, W. A. Hendrickson, J. Sodroski, *Science* 280, 1949 (1998); D. S. Dimitrov, *Cell* 91, 721 (1997); E. A. Berger, P. M. Murphy, J. M. Farber, *Annu. Rev. Immunol.* 17, 657 (1999).
3. Q. J. Sattentau and J. P. Moore, *J. Exp. Med* 174, 407 (1991); T. K. Hart, R. Kirsch, H. Ellens, R. W. Sweet, D. M. Lambert, S. R. Pettway, Jr., J. Learly, P. J. Bugelski, *Proc. Natl. Acad. Sci. USA* 88, 2189 (1991); Q. J. Sattentau and J. P. Moore, *J. Virol.* 67, 7383 (1993); Q. J. Sattentau, J. P. Moore, F. Vignaux, F. Traincard, P. Poignard, *J. Virol.* 67, 7383 (1993); N. Sullivan, Y. Sun, J. Li, W. Hofmann, J. Sodroski, *J. Virol.* 69, 4413 (1995); L. Stamatatos and C. Cheng-Mayer, *J. Virol.* 69, 6191 (1995); A. Trkola, T. Dragic, J. Arthos, J. M. Binley, W. C. Olson, G. P. Allaway, C. Cheng-Mayer, J. Robinson, P. J. Maddon, J. P. Moore, *Nature* 384, 184 (1996); L. Wu, N. P. Gerard, R. Wyatt, H. Choe, C. Parolin, N. Ruffing, A. Borsett, A. A. Cardoso, E. Desjardin, W. Newman, C. Gerard, J. Sodroski, *Nature* 384,179 (1996); D. R. Littman, *Cell* 93, 677 (1998); N. Sullivan, Y. Sun, Q. J. Sattentau, M. Thali, D. Wu, G. Denisova, J. Gershoni, J. Robinson, J. P. Moore, J. Sodroski, *J. Virol.* 72, 4694 (1998); J. S. Allan, J. Strauss, D. W. Buck, *Science* 247, 1084 (1990).
4. C. M. Carr and P. S. Kim, *Cell* 73, 823 (1993); P. A. Bullough, F. M. Hughson, J. J. Skehel, D. C. Wiley, *Nature* 371, 37 (1994); J. Chen, S. A. Wharton, W. Weissenhorn, L. J. Calder, F. M. Hughson, J. J. Skehel, D. C. Wiley, *Proc. Natl. Acad. Sci. USA* 92, 12205 (1995); C. M. Carr, C. Chaudhry, P. S. Kim, *Proc. Natl. Acad. Sci. USA* 94, 14306 (1997).
5. See, for example, D. C. Chan and P. S. Kim, *Cell* 93, 681 (1998); R. Wyatt and J. Sodroski, *Science* 280, 1884 (1998); J. P. Moore, B. A. Jameson, R. A. Weiss, Q. J. Sattentau, in *Viral Fusion Mechanisms*, J. Bentz, J. Ed. (CRC Press, Boca Raton, 1993), pp. 233–289.
6. D. C. Chan, D. Fass, J. M. Berger, P. S. Kim, *Cell* 89, 263 (1997); W. Weissenhom, A. Dessen, S. C. Harrison, J. J. Skehel, D. C. Wiley, *Nature* 387, 426 (1997); K. Tan, J. H. Liu, J. H. Wang, S. Shen, M. Lu, *Proc. Natl. Acad. Sci. USA* 94, 12303 (1997); M. Caffrey, M. Cai, J. Kaufman, S. J. Stahl, P. T. Wingfield, D. G. Covell. A. M. Gronenborn, G. M. Clore, *EMBO J.* 17, 4572 (1998); Z. N. Yang, T. C. Mueser, J. Kaufman, S. J. Stahl, P. T. Wingfield, C. C. Hyde, *J. Struct. Biol.* 126, 131 (1999).
7. W. Weissenhorn, A. Dessen, S. C. Harrison, J. J. Skehel, D. C. Wiley, *Nature* 387, 426 (1997); F. M. Hughson, *Curr. Biol.* 7, R565 (1997); R. A. Furuta, C. T. Wild, Y. Weng, C. D. Weiss, *Nature Struct. Biol.* 5, 276 (1998).
8. S. Jiang, K. Lin, M. Lu, *J. Virol.* 72, 10213 (1998).
9. See, for example, C. T. Wild, T. Oas, C. B. McDanal, D. Bolognesi, T. J. Matthews, *Proc. Natl. Acad. Sci. USA* 89, 10537 (1992); J. G. Sodroski, *Cell* 99, 243 (1999); J. K. Judice, J. Y. K. Tom, W. Huang, T. Wrin, J. Vennari, C. J. Petropoulos, R. S. McDowell, *Proc. Natl. Acad. Sci. USA* 94, 13426 (1997); R. A. LaCasse, K. E. Follis, M. Trahey, J. D. Scarborough, D. R. Littman, J. H. Nunberg, *Science* 283, 357 (1999).
10. C. D. Weiss, J. A. Levy, J. M. White, *J. Virol.* 64, 5674 (1990); H. R. Gelderblom, M. Özel, E. H. S. Hausmann, T. Winkel, G. Pauli, M. A. Koch, *Micron. Microsc. Acta* 19, 41 (1988); P. L. Earl, R. W. Doms, B. Moss, *Proc.*

*Natl. Acad. Sci. USA* 87, 648 (1990); J. W. Dubay, S. J. Roberts, B. Brody, E. Hunter, *J. Virol.* 66, 4748 (1992); S. S. Chen, C. N. Lee, W. R. Lee, K. McIntosh, T. H. Lee, *J. Virol.* 67, 3615 (1993); S. S. Chen, *J. Virol.* 68, 2002 (1994); C. T. Wild, J. W. Dubay, T. K. Greenwell, T. Baird, T. G. Oas, C. B. McDanal, E. Hunter, T. J. Matthews, *Proc. Natl. Acad. Sci. USA* 91, 12676 (1994); P. Poumbourios, K. A. Wilson, R. J. Center, W. ElAhmar, B. E. Kemp, *J. Virol.* 71, 2041 (1997); Y. Weng and C. D. Weiss, *J. Virol.* 72, 9676 (1998).
11. H. R. Gelderblom, H. Reupke, G. Pauli, *Lancet* ii, 1016 (1985); V. S. Kalyanaraman, V. Rodriguez, F. Veronese, R. Rahman, P. Lusso, A. L. DeVico, T. Copeland, S. Oroszlan, R. C. Gallo, M. G. Sarngadharan, *AIDS Res. Hum. Retroviruses* 6, 371 (1990); J. P. Moore, J. A. McKeating, R. A. Weiss, Q. J. Sattentau, *Science* 250, 1139 (1990); E. Helseth, U. Olshevsky, U. Furman, J. Sodroski, *J. Virol.* 65, 2119 (1991); J. A. McKeating, A. McKnight, J. P. Moore, *J. Virol.* 65, 852 (1991); P. Poignard, T. Fouts, D. Naniche, J. P. Moore, Q. J. Sattentau, *J. Exp. Med.* 183, 473 (1996).
12. C. T. Wild, J. W. Dubay, T. K. Greenwell, T. Baird, T. G. Oas, C. B. McDanal, E. Hunter, T. J. Matthews, *Proc. Natl. Acad. Sci. USA* 91, 12676 (1994); M. Lu, H. Ji, S. Shen, *J. Virol.* 73, 4433 (1999).
13. F. H. C. Crick, *Acta Crystallogr.* 6, 689 (1953).
14. P. B. Harbury, P. S. Kim, T. Alber, *Nature* 371, 80 (1994).
15. M. Lu, S. C. Blacklow, P. S. Kim, *Nature Struct. Biol.* 2, 1075 (1995).
16. R. A. Furuta, C. T. Wild, Y. Weng, C. D. Weiss, *Nature Struct. Biol.* 5, 276 (1998); P. L. Jones, T. Korte, R. Blumenthal, *J. Biol. Chem.* 273, 404 (1998); I. Munoz-Barroso, S. Durell, K. Sakaguchi, E. Appella, R. Blumenthal, *J. Cell Biol.* 140, 315 (1998).
17. J. Cao, L. Bergeron, E. Helseth, M. Thali, H. Repke, J. Sodroski, *J. Virol.* 67, 2747 (1993).
18. W. Shu, J. Liu, H. Ji, L. Radigen, S. Jiang, M. Lu, *Biochemistry* 39, 1634 (2000).
19. T. Stegmann, J. M. Delfino, F. M. Richards, A. Helenius, *J. Biol. Chem.* 266, 18404 (1991); M. Tsurudome, R. Glück, R. Graf, R. Falchetto, U. Schaller, J. Brunner, *J. Biol. Chem.* 267, 20225 (1992); J. M. White, *Science* 258, 917 (1992).
20. Reviewed in J. J. Skehel and D. C. Wiley, *Cell* 95, 871 (1998).
21. J. Sodroski, W. C. Goh, C. Rosen, K. Campbell, W. A. Haseltine, *Nature* 322, 470 (1986); S. S. Chen, *J. Virol.* 68, 2002 (1994); J. M. Binley, R. W. Sanders, B. Clas, N. Schuelke, A. Master, Y. Guo, F. Kajurno, D. J. Anselma, P. J. Maddon, W. C. Olson, J. P. Moore, *J. Virol.* 74, 627 (2000).
22. S. Jiang, K. Lin, N. Strick, A. R. Neurath, *Nature* 365, 113 (1993); C. T. Wild, D. C. Shugars, T. K. Greenwell, C. B. McDanal, T. J. Matthews, *Proc. Natl. Acad. Sci. USA* 91, 9770 (1994).
23. J. M. Kilby, S. Hopkins, T. M. Venetta, B. DiMassimo, G. A. Cloud, J. Y. Lee, Y. Alldredge, E. Hunter, D. Lambert, D. Bolognesi, T. Matthews, M. R. Johnson, M. A. Nowak, G. M. Shaw, M. S. Saag, *Nature Med.* 4, 1302 (1998).
24. C. H. Chen, T. J. Matthews, C. B. McDanal, D. P. Bolognesi, M. L. Greenberg, *J. Virol.* 69, 3771 (1995); C. Wild, T. Greenwell, D. Shugars, L. Rimsky-Clarke, T. Matthews, *AIDS Res. Hum. Retroviruses* 11, 323 (1995); L. T. Rimsky, D. C. Shugars, T. J. Matthews, *J. Virol.* 72, 986 (1998); D. C. Chan, C. T. Chutkowski, P. S. Kim, *Proc. Natl. Acad. Sci. USA* 95, 15613 (1998).
25. D. M. Eckert, V. N. Malashkevich, L. H. Hong, P. A. Carr, P. S. Kim, *Cell* 99, 103 (1999); M. Ferrer, T. M. Kapoor, T. Strassmaier, W. Weissenhorn, J. J. Skehel, D. Oprian, S. Schreiber, D. C. Wiley, S. C. Harrison, *Nature Struct. Biol.* 6, 953 (1999).
26. UNAIDS Report (available at www.unaids.org/highband/document/epidemio/wadr99e.pdf).
27. T. E. Mertens and A. Burton, *AIDS* 10 (suppl. A), S221 (1996); C. A. Heillman and D. Baltimore, *Nature Med.* 4, 532 (1998); M. R. Hilleman, *Vaccine* 16, 778 (1998).
28. B. F. Haynes, G. Pantaleo, A. S. Fauci, *Science* 271, 324 (1996); D. R. Burton and D. C. Montefiori, *AIDS* 11 (suppl A), 587 (1997); S. Rowland-Jones, R. Tan, A. McMichael, *Adv. Immunol.* 65, 448 (1997); D. R. Burton and J. P. Moore, *Nature Med.* 4, 495 (1998); N. L. Letvin, *Science* 280, 1875 (1998); D. C. Montefiori and T. G. Evans, *AIDS Res. Hum. Retroviruses* 15, 689 (1999).
29. R. Shibata, T. Igarashi, N. Haigwood, A. Buckler-White, R. Ogert, W. Ross, R. Willey, M. W. Cho, M. A. Martin, *Nature Med.* 5, 204 (1999); T. Igarashi, C. Brown, A. Azadegan, N. Haigwood, D. Dimitrov, M. A. Martin, R. Shibata, *Nature Med.* 5, 211 (1999).
30. Reviewed in D. R. Burton, *Proc. Natl. Acad. Sci. USA* 94, 10018 (1997).
31. Reviewed in E. A. Berger, P. M. Murphy, J. M. Farber, *Annu. Rev. Immunol.* 17, 657 (1999); J. P. Moore, A. Trkola, T. Dragic, *Curr. Opin. Immunol.* 9, 551 (1997); B. J. Doranz, J. F. Berson, J. Bucker, R. W. Doms, *Immunol. Res.* 16, 15 (1997).
32. Reviewed in D. C. Chan and P. S. Kim, *Cell* 93,681 (1998); J. J. Skehel and D. C. Wiley, *Cell* 95, 871 (1998).
33. D. C. Chan, D. Fass, J. M. Berger, P. S. Kim, *Cell* 89, 263 (1997); W. Weissenhorn, A. Dessen, S. C. Harrison, J. J. Skehel, D. C. Wiley, *Nature* 387, 426 (1997); K. Tan, J. H. Liu, J. H. Wang, S. Shen, M. Lu, *Proc. Natl. Acad. Sci. USA* 94, 12303 (1997).
34. B. F. Haynes, *Lancet* 348,933 (1996); S. Jiang, K. Lin, M. Lu, *J. Virol.* 72, 10213 (1998).
35. P. W. Parren, D. R. Burton, Q. J. Sattentau, *Nature Med.* 3, 366 (1997).
36. M. P. D'Souza, D. Livnat, J. A. Bradac, S. Bridges, The AIDS Clinical Trials Group Antibody Selection Working Group, and Collaborating Investigators. *J. Infect. Dis.* 175, 1056 (1997); T. R. Fouts, J. M. Binley, A. Trkola, J. E. Robinson, J. P. Moore, *J. Virol.* 71, 2779 (1997).
37. J. A. McKeating, A. McKnight, J. P. Moore, *J. Virol.* 65, 852 (1991); R. L. Willey, M. A. Martin, K. W. Peden, *J. Virol.* 68, 1029 (1994).
38. R. A. LaCasse, K. E. Follis, M. Trahey, J. D. Scarborough, D. R. Littman, J. H. Nunberg, *Science* 283, 357 (1999). P. W. H. I. Parren, J. P. Moore, D. R. Burton, Q. J. Sattentau, *J. Acquir. Immune Defic. Syndr.* 13 (suppl A), S137 (1999); N. Sullivan, Y. Sun, Q. Sattentau, M. Thali, D. Wu, G. Denisova, J. Gershoni, J. Robinson, J. P. Moore, J. Sodroski, *J. Virol.* 72, 4694 (1998); J. Cao, N. Sullivan, E. Desjardin, C. Parlin, J. Robinson, R. Wyatt, J. Sodroski, *J. Virol.* 71, 9808 (1997); T. M. Richardson, Jr., B. L. Stryjewski, C. C. Broder, J. A. Hoxie, J. R. Mascola, P. L. Earl, R. W. Doms, *J. Virol.* 70, 753 (1996);
39. T. Muster, F. Steindl, M. Purtscher, A. Trkola, A. Klima, G. Himmler, F. Rüker, H. Katinger, *J. Virol.* 67, 6642 (1993); T. Muster, R. Guinea, A. Trkola, M. Purtscher, A. Klima, F. Steindl, P. Palese, H. Katinger, *J. Virol.* 68, 4031 (1994); Q. J. Sattentau, S. Zolla-Pazner, P. Poignard, *Virology* 206, 713 (1995).

SEQUENCE LISTING

<160> NUMBER OF SEQ ID NOS: 9

<210> SEQ ID NO 1
<211> LENGTH: 46
<212> TYPE: PRT
<213> ORGANISM: Artificial Sequence
<220> FEATURE:
<223> OTHER INFORMATION: The amino acid sequence of the COOH-terminal
      extension of gp41.

<400> SEQUENCE: 1

Asn Glu Gln Glu Leu Leu Glu Leu Asp Lys Trp Gly Thr Lys Ile Lys
 1               5                  10                  15

Gln Ile Glu Asp Lys Ile Glu Glu Ile Leu Ser Lys Ile Tyr His Ile
            20                  25                  30

Glu Asn Glu Ile Ala Arg Ile Lys Lys Leu Ile Gly Glu Arg
        35                  40                  45

<210> SEQ ID NO 2
<211> LENGTH: 78
<212> TYPE: PRT
<213> ORGANISM: Artificial Sequence
<220> FEATURE:
<223> OTHER INFORMATION: Linear amino acid sequence of a helical wheel
      projection of C45-pII.

<400> SEQUENCE: 2

Asn His Thr Thr Trp Leu Glu Trp Asp Arg Glu Ile Asn Asn Tyr Thr
 1               5                  10                  15

Ser Leu Ile His Ser Leu Ile Glu Glu Ser Gln Asn Gln Gln Glu Lys
            20                  25                  30

Asn Glu Gln Glu Leu Leu Glu Leu Asp Lys Trp Ala Ser Lys Ile Lys
        35                  40                  45

Gln Ile Glu Asp Lys Ile Glu Glu Ile Leu Ser Lys Ile Tyr His Ile
    50                  55                  60

Glu Asn Glu Ile Ala Arg Ile Lys Lys Leu Ile Gly Glu Arg
65                  70                  75

<210> SEQ ID NO 3
<211> LENGTH: 52
<212> TYPE: PRT
<213> ORGANISM: Artificial Sequence
<220> FEATURE:
<223> OTHER INFORMATION: Amino acid sequence of C52.

<400> SEQUENCE: 3

Asn His Thr Thr Trp Leu Glu Trp Asp Arg Glu Ile Asn Asn Tyr Thr
 1               5                  10                  15

Ser Leu Ile His Ser Leu Ile Glu Glu Ser Gln Asn Gln Gln Glu Lys
            20                  25                  30

Asn Glu Gln Glu Leu Leu Glu Leu Asp Lys Trp Ala Ser Leu Trp Asn
        35                  40                  45

Trp Phe Asn Ile
    50

<210> SEQ ID NO 4
<211> LENGTH: 85
<212> TYPE: PRT
<213> ORGANISM: Artificial Sequence
<220> FEATURE:
<223> OTHER INFORMATION: The chimera of the C52 peptide and an -continued isoleucine-zipper trimer (GCN4-pII).
<400> SEQUENCE: 4

Asn His Thr Thr Trp Leu Glu Trp Asp Arg Glu Ile Asn Asn Tyr Thr
1               5                   10                  15

Ser Leu Ile His Ser Leu Ile Glu Glu Ser Gln Asn Gln Gln Glu Lys
            20                  25                  30

Asn Glu Gln Glu Leu Leu Glu Leu Asp Lys Trp Ala Ser Leu Trp Asn
        35                  40                  45

Trp Phe Asn Ile Lys Ile Lys Gln Ile Glu Asp Lys Ile Glu Glu Ile
    50                  55                  60

Leu Ser Lys Ile Tyr His Ile Glu Asn Glu Ile Ala Arg Ile Lys Lys
65                  70                  75                  80

Leu Ile Gly Glu Arg
                85

<210> SEQ ID NO 5
<211> LENGTH: 7
<212> TYPE: PRT
<213> ORGANISM: Artificial Sequence
<220> FEATURE:
<223> OTHER INFORMATION: Most common sequence of amino acids at
      positions 669-675 of gp160 (M group HIV-1 strain).

<400> SEQUENCE: 5

Leu Trp Asn Trp Phe Asp Ile
1               5

<210> SEQ ID NO 6
<211> LENGTH: 6
<212> TYPE: PRT
<213> ORGANISM: Artificial Sequence
<220> FEATURE:
<223> OTHER INFORMATION: Amino acid sequence immediately NH2-terminal
      to SEQ ID NO:5.

<400> SEQUENCE: 6

Glu Leu Asp Lys Trp Ala
1               5

<210> SEQ ID NO 7
<211> LENGTH: 7
<212> TYPE: PRT
<213> ORGANISM: Artificial Sequence
<220> FEATURE:
<223> OTHER INFORMATION: Amino acids 669-675 of gp41.

<400> SEQUENCE: 7

Leu Trp Asn Trp Phe Asn Ile
1               5

<210> SEQ ID NO 8
<211> LENGTH: 7
<212> TYPE: PRT
<213> ORGANISM: Artificial Sequence
<220> FEATURE:
<223> OTHER INFORMATION: Amino acids at positions 669-675 of gp160.
<220> FEATURE:
<221> NAME/KEY: SITE
<222> LOCATION: 1
<223> OTHER INFORMATION: Xaa = Leu, Ile, Val, or Ser.
<220> FEATURE:
<221> NAME/KEY: SITE
<222> LOCATION: 2
<223> OTHER INFORMATION: Xaa = tryptophan or no amino acid present due
      to the presence of a stop codon at this position in the reading
      frame.

```
<220> FEATURE:
<221> NAME/KEY: SITE
<222> LOCATION: 3
<223> OTHER INFORMATION: Xaa = Asn, Ser, Thr, or Asp or no amino acid
      present due to the presence of a stop codon at an earlier
      position in the reading frame.
<220> FEATURE:
<221> NAME/KEY: SITE
<222> LOCATION: 4
<223> OTHER INFORMATION: Xaa = Trp or no amino acid present due to the
      presence of a stop codon at this position or at an earlier
      position in the reading frame.
<220> FEATURE:
<221> NAME/KEY: SITE
<222> LOCATION: 5
<223> OTHER INFORMATION: Xaa = Phe, Leu, Tyr, or Ser or no amino acid
      present due to the presence of a stop codon at an earlier
      position in the reading frame.
<220> FEATURE:
<221> NAME/KEY: SITE
<222> LOCATION: (6)...(6)
<223> OTHER INFORMATION: Xaa = Asp, Ser, Asn, Gly, Thr, Glu, or no amino
      acid present due to the presence of a stop codon at this position
      or an earlier position in the reading frame.
<220> FEATURE:
<221> NAME/KEY: SITE
<222> LOCATION: (7)...(7)
<223> OTHER INFORMATION: Xaa = Ile or Met or no amino acid present due
      to the presence of a stop codon at an earlier position in the
      reading frame.

<400> SEQUENCE: 8

Xaa Xaa Xaa Xaa Xaa Xaa Xaa
 1               5

<210> SEQ ID NO 9
<211> LENGTH: 52
<212> TYPE: PRT
<213> ORGANISM: Artificial Sequence
<220> FEATURE:
<223> OTHER INFORMATION: Mutant (N656L) amino acid sequence of C52.

<400> SEQUENCE: 9

Asn His Thr Thr Trp Leu Glu Trp Asp Arg Glu Ile Asn Asn Tyr Thr
 1               5                  10                  15

Ser Leu Ile His Ser Leu Ile Glu Glu Ser Gln Asn Gln Gln Glu Lys
            20                  25                  30

Leu Glu Gln Glu Leu Leu Glu Leu Asp Lys Trp Ala Ser Leu Trp Asn
        35                  40                  45

Trp Phe Asn Ile
    50
```

What is claimed is:

1. A stabilized viral envelope protein comprising three parallel, α-helical COOH-terminal viral envelope glycoprotein monomers that together form a stable three-stranded coiled coil having a conformation like that of a native form of the viral envelope glycoprotein when associated with a cellular membrane, wherein the stabilized viral envelope protein is substantially incapable of undergoing a conformational change to become active for membrane fusion, and wherein the monomer comprises SEQ ID NO:3, 5, 7 or 9 fused to a GCN-4pII peptide comprising residues 53 to 85 of SEQ ID NO:4.

2. A stabilized viral envelope protein comprising three parallel, α-helical COOH-terminal viral envelope glycoprotein monomers that together form a stable three-stranded coiled coil having a conformation like that of a native form of the viral envelope glycoprotein when associated with a cellular membrane, wherein the stabilized viral envelope protein is substantially incapable of undergoing a conformational change to become active for membrane fusion, and wherein the monomer comprises SEQ ID NO:1, 2 or 4.

3. The stabilized viral envelope protein of claim 1, wherein the native form of a viral envelope glycoprotein is an HIV1 or HIV2 viral envelope glycoprotein.

4. The stabilized viral envelope protein of claim 1, wherein the native form of a viral envelope glycoprotein comprises three HIV gp41 monomers that form a trimeric coiled coil, in a prefusogenic conformation.

5. The stabilized viral envelope protein of claim 1, wherein the monomer is recombinantly produced.

6. The stabilized viral envelope protein of claim 1, wherein the monomer is synthetically produced.

7. The stabilized viral envelope protein of claim 1, wherein the three-stranded coiled coil is stabilized by one or more point mutations.

8. The stabilized viral envelope protein of claim 7, wherein the three-stranded coiled coil with one or more point mutations has SEQ ID NO:9.

9. The stabilized viral envelope protein of claim 1, wherein the three-stranded coiled coil is stabilized by chemical cross-linking.

10. The stabilized viral envelope protein of claim 4, wherein the gp41 monomers comprise SEQ ID NO:7.

11. The stabilized viral envelope protein of claim 4, wherein the gp41 monomers comprise SEQ ID NO:3 or SEQ ID NO:4.

* * * * *

UNITED STATES PATENT AND TRADEMARK OFFICE
CERTIFICATE OF CORRECTION

PATENT NO. : 7,179,468 B1 Page 1 of 1
APPLICATION NO. : 09/877606
DATED : February 20, 2007
INVENTOR(S) : Lu et al.

It is certified that error appears in the above-identified patent and that said Letters Patent is hereby corrected as shown below:

On the title page, item (57), under "Abstract", in column 2, line 6, after "virus" insert -- , --.

On the title page, item (57), under "Abstract", in column 2, line 7, delete "vacciness" and insert -- vaccines --, therefor.

On the title page, item (57), under "Abstract", in column 2, line 7, delete "virus," and insert -- viruses --, therefor.

In column 29, line 61, in Claim 1, delete "GCN-4pII" and insert -- GCN-4-pII --, therefor.

Signed and Sealed this

Twenty-ninth Day of July, 2008

JON W. DUDAS
*Director of the United States Patent and Trademark Office*